(12) United States Patent
Finch et al.

(10) Patent No.: US 7,564,027 B2
(45) Date of Patent: Jul. 21, 2009

(54) ADSORPTION, DETECTION AND IDENTIFICATION OF COMPONENTS OF AMBIENT AIR WITH DESORPTION/IONIZATION ON SILICON MASS SPECTROMETRY (DIOS-MS)

(75) Inventors: Jeffrey W. Finch, Mendon, MA (US); Chris L. Stumpf, Milford, MA (US); Bruce J. Compton, Lexington, MA (US)

(73) Assignee: Waters Investments Limited, New Castle, DE (US)

( * ) Notice: Subject to any disclaimer, the term of this patent is extended or adjusted under 35 U.S.C. 154(b) by 451 days.

(21) Appl. No.: 10/545,332

(22) PCT Filed: Feb. 9, 2004

(86) PCT No.: PCT/US2004/003719

§ 371 (c)(1),
(2), (4) Date: Jul. 28, 2006

(87) PCT Pub. No.: WO2005/029003

PCT Pub. Date: Mar. 31, 2005

(65) Prior Publication Data

US 2007/0023627 A1     Feb. 1, 2007

Related U.S. Application Data

(60) Provisional application No. 60/474,457, filed on May 30, 2003, provisional application No. 60/446,453, filed on Feb. 10, 2003, provisional application No. 60/446,383, filed on Feb. 10, 2003.

(51) Int. Cl.
*H01J 49/00* (2006.01)

(52) U.S. Cl. .......... 250/288; 250/286; 250/282; 250/340; 250/341.1; 250/341.2; 250/281; 250/423 R; 250/284; 250/290; 435/6; 435/287.2; 435/7.1; 435/287.1; 435/288.7; 428/357; 428/364; 428/304.4; 428/446; 428/195.1; 436/86; 436/173; 436/174; 436/525; 436/518; 427/2.11; 422/82.05; 422/82.01; 356/301; 356/244

(58) Field of Classification Search ........... 250/288, 250/286, 282, 340, 341.1, 341.2, 281, 423 R, 250/284, 290; 435/6, 287.2, 7.1, 287.1, 288.7; 428/357, 364, 367, 304.4, 446, 195.1; 436/86, 436/173, 174, 525, 518; 427/2.11; 422/82.05, 422/82.01; 356/301, 244

See application file for complete search history.

(56) References Cited

U.S. PATENT DOCUMENTS

| | | |
|---|---|---|
| 4,541,268 A | 9/1985 | Odemheimer |
| 4,701,306 A | 10/1987 | Lawrence et al. |
| 4,912,051 A | 3/1990 | Zaromb |
| 4,977,095 A | 12/1990 | Zaromb |
| 5,005,399 A | 4/1991 | Holtzclaw et al. |
| 5,173,264 A | 12/1992 | Zaromb et al. |
| 5,376,788 A | 12/1994 | Standing et al. |
| 5,595,709 A | 1/1997 | Klemp |
| 5,719,060 A | 2/1998 | Hutchens et al. |
| 5,795,368 A | 8/1998 | Wright et al. |
| 5,859,431 A | 1/1999 | Cotrell et al. |
| 5,872,306 A | 2/1999 | Arnold |
| 5,882,496 A | 3/1999 | Northrup et al. |
| 5,954,860 A | 9/1999 | Gordon |
| 6,020,208 A | 2/2000 | Hutchens et al. |
| 6,124,137 A | 9/2000 | Hutchens et al. |
| 6,288,390 B1 * | 9/2001 | Siuzdak et al. ............ 250/288 |
| 6,358,613 B1 | 3/2002 | Buriak |
| 6,391,551 B1 | 5/2002 | Shultz et al. |
| 2002/0048531 A1 | 4/2002 | Fonash et al. |
| 2003/0057106 A1 | 3/2003 | Zhouxin et al. |

FOREIGN PATENT DOCUMENTS

| | | |
|---|---|---|
| EP | 0 617 048 A1 | 9/1994 |
| GB | 0515890.2 | 2/2007 |

WO WO-00/54309 A1 9/2000

OTHER PUBLICATIONS

William A. McClenny, et al., "*Canister-Based Method for Monitoring Toxic VOCs in Ambient Air*"; J. Air Waste Management Association; vol. 41; No. 10; Oct. 1991; pp. 1308-1318.

R. M. Riggin; "*Compendium of Methods for the Determination of Toxic Organic Compounds in Ambient Air EPA Methods TO-1 and TO-2*"; U.S. Environmental Protection Agency., Research Triangle Park, NC 27711, EPA 600/4-84-041, Apr. 1984.

William T. Winberry, Jr., et al.; "*Compendium of Methods for the Determination of Toxcic Organic Compounds in Ambient Air: EPA Methods TO-14, Second Supplement*"; U.S. Environmental Protection Agency, Research Triangle Park, NC 27711, EPA 600/4-89-018, Mar. 1989.

Annon.; "Compendium of Methods for the Determination of Toxic Organic Compounds in Ambient Air, Second Edition: EPA Method TO-17"; U.S. Environmental Protection Agency, Cincinnati, OH 45268, EPA/625/R-96O1Ob; Jan. 1997.

Elizabeth Woolfenden; Monitoring VOCs in Air Using Sobent Tubes Followed by Thermal Desorption-Capillary GC Analysis: Summary of Data and Practical Guidelines:; Journal of the Air & Waste Management Association; vol. 47; Jan. 1997; pp. 20-36.

James F. Pankow; "Determination of a Wide Range of Volatile Organic Compounds in Ambient Air Using Multisorbent Adsorption/Thermal Desorption and Gas Chromatography/Mass Spectrometry"; Analytical Chemistry; vol. 70; No. 4; Dec. 15, 1998; pp. 5213-5221.

P. Ciccioli et al.; "Gas Chromatographic Evaluation of the Organic Components Present in the Atmosphere at Trace Levels with the Aid of Carbopack B for Pre-Concentration of the Sample"; Journal of Chromatography; 351; (1986); pp. 433-449.

R. H. Brown et al.; "Collection and Analysis of Trace Organic Vapour Pollutants in Ambient Atmospheres: The Performance A Tenac-GC Adsorbent Tube"; Journal of Chromatography; 178; (1979); pp. 79-90.

J. F. Walling; "The Utility of Distributed Air Volume Sets When Sampling Ambient Air Using Solid Adsorbents"; Atmospheric Environment; vol. 18; No. 4; (1984) pp. 855-859.

James F. Pankow, et al.; "Determination of Volatile Compounds in Water by Purging Directly to a Capillary Column with Whole Column Cryotrapping"; Environ. Sci. Technol.; vol. 22; No. 4; (1988); pp. 398-405.

B. A. Ewels, et al.; "*Electrically Heated Cold Trap Inlet System for High-Speed Gas Chromatography*"; American Chemical Society; vol. 57; (1985); pp. 2774-2779.

Robert F. Mouradian, et al.; "Evaluation of a Nitrogen-Cooled, Electrically Heated Cold Trap Inlet for High-Speed Gas Chromatography"; Journal of Chromatographic Science; vol. 28; Dec. 1990; pp. 643-648.

Mark A. Klemp, et al.; "*Cryofocusing Inlet with Reverse Flow Sample Collection for Gas Chromatography*"; American Chemical Society; vol. 65; (1993); pp. 2516-2521.

Robert Tijssen, et al.; "Theoretical Aspects and Practical Potentials of Rapid Gas Analysis in Capillary Gas Chromatography"; American Chemical Society; vol. 59; (1987); pp. 1007-1015.

PCT International Search Report and Written Opinion.

Wei, J., et al., Desorption-Ionization Mass Spectrometry on Porous Silicon Nature, 1999, vol. 399, pp. 243-246.

Buriak & Allen. "Lewis Acid Mediated Functionalization of Porous Silicon with Substituted Alkenes and Alkynes", J. Am. Chem. Soc. 1998, 120, 1339-1340.

D. J. Rousell et al., "Modification of a Commeridal Mass Spectrometer for Employment of Infrared Desorption/Ionisation of Silicon", Poster Abstract P35-T, Presented at ABRF Symposium, Feb. 10-13, 2003.

\* cited by examiner

*Primary Examiner*—Jack I Berman
*Assistant Examiner*—Meenakshi S Sahu
(74) *Attorney, Agent, or Firm*—Edwards Angell Palmer & Dodge LLP; Peter C. Lauro, Esq.

(57) ABSTRACT

The present invention provides a device, system, and associated methods to actively or passively sample air by directing it onto the surface of a porous light-absorbing semiconductor, for example, a desorption/ionization on porous silicon ("DIOS") chip. Upon adsorption of an analyte, the surface may be analyzed directly by laser desorption/ionization time-of-flight mass spectrometry. Because the process of laser desorption/ionization and subsequent mass detection does not require elevated temperatures, thermal degradation of analytes is avoided.

20 Claims, 5 Drawing Sheets

ADSORPTION, DETECTION AND IDENTIFICATION OF COMPONENTS OF AMBIENT AIR WITH DESORPTION/IONIZATION ON SILICON MASS SPECTROMETRY (DIOS-MS)

RELATED APPLICATIONS

This application is a U.S. national phase application, pursuant to 35 U.S.C. §371, of PCT international application Ser. No. PCT/US2004/003719 filed Feb. 9, 2004, designating the United States, which claims priority under 35 U.S.C. §119 to U.S. provisional patent application Ser. No. 60/446,383 filed Feb. 10, 2003, U.S. provisional patent application Ser. No. 60/446,453 filed Feb. 10, 2003 and U.S. provisional patent application Ser. No. 60/474,457 filed May 30, 2003. The entire contents of the aforementioned patent applications are incorporated herein by this reference.

BACKGROUND

The measurement and detection of components of gases, particularly ambient air, are important in environmental monitoring, forensics, and as a research tool.

In one simple technique, a colorimetric indicator containing a specific solid that absorbs components from a gas and reacts with it, qualitatively detects the presence of certain analytes by producing a characteristic color change. For example, indicator devices are commercially available that detect the presence of toxic chemicals such as carbon monoxide and hydrogen sulfide. Although such calorimetric devices are usually inexpensive, they are not useful in the detection of gas components generally because they are limited by the reactivity of the solid indicator material for the complementary specific chemicals for which they were designed. Furthermore, colorimetric indicators are generally not capable of quantitative measurement.

Other techniques of more general utility permit the detection and measurement of components of gas samples, including low concentration components. Frequently, the detection of low concentration components of gases is limited by the sensitivity of instruments. In order to improve low concentration measurements, gas-borne analytes may be concentrated prior to detection. Typically, a three step process is used to study the components of a gas sample: collection of the gas sample, pre-concentration of the analytes therein, and detection of the analytes. For example, a gas sample may be collected by an evacuated canister of about 6 to 12 liters (or larger) that, upon opening a control valve, sucks in ambient air. The ambient air is then returned to the laboratory for analysis. See, e.g., McClenny, et al., "Canister-based method for monitoring toxic VOCs in ambient air," J. Air Waste Manage. Assoc. 41, 1308-18 (1991). More conveniently, however, the steps of collection of the gas sample, and pre-concentration and detection of analytes are often performed simultaneously.

One method of pre-concentrating analytes from the gaseous phase involves passing a sample gas through a liquid suitable for dissolving the analytes. For example, a pollutant gas may be collected by bubbling it through a liquid in which the pollutant dissolves. Typically, ambient air enters an extraction device through a moisture trap and filter, and then it is contacted with a liquid extraction medium, which is then analyzed to determine the concentration of gaseous pollutant. When used with continuous-feed mechanisms, large gas volumes may be extracted and analyzed. Gas-liquid extraction methods are not widely used because they typically require large volumes of solvent, expensive machinery, and lengthy analysis times.

A more common method of pre-measurement concentration uses "adsorption" (or "diffusion") tubes containing a "sorbent" material, e.g., activated charcoal, that selectivity retains and desorbs toxic chemicals, contaminants, or other substances of interest from a gas sample. A pump may move a gas sample through a pre-concentrator tube containing a sorbent material that retains analytes of interest until a sufficiently large sample accumulates. A heating element wrapped around the pre-concentrator tube is then used to heat the sorbent material and thereby desorb or volatilize the chemicals. Upon desorption, the chemicals are conducted to a measurement instrument that indicates the presence, identity, or amount of the various chemicals.

Certain solids are capable of retaining specific analytes on their surface. Activated carbon or charcoal is often used to retain and concentrate organic chemicals from air streams. Various other sorbent materials may also be used, depending on the nature of the analytes of interest. For example, one material useful in the analysis of amines includes a mixture of an adsorbent organic polymer having an affinity for amines, e.g., Tenax® (2,6-diphenylphenylene oxide polymer, a registered trademark of Buchem, N.V.), and a second adsorbent that is an inorganic porous material and is alkaline, e.g., soda lime. U.S. Pat. No. 4,701,306.

Typically, sorbent-based techniques are solid phase extraction methods that use a flow-through chamber containing a stationary phase material to preferentially retain components of interest from a gas sample flushed through the cartridge. A solvent in which the retained analytes are soluble is then flushed through the cartridge, thereby producing a solution of components of interest for analysis. Several adsorption tubes are commercially available, including those filled with a variety of stationary phase adsorbent materials such as activated carbon, graphitized carbon black, silica gel, quartz glass, carbon molecular sieves, or poly(2,6-diphenylphenylene oxide). Although solvent-wetted sorbent materials have also been used to pre-concentrate analytes from vapors or aerosols, U.S. Pat. Nos. 5,173,264, 4,912,051, and 4,977,095, dry sorbent materials are more commonly used.

EPA Methods TO-1, -5, and -17, for example, are sorbent-based methods for the measurement of volatile organic compounds in ambient air. In these EPA methods, a sample is passed through a cartridge containing an adsorbent such as Tenax®, XAD-2 (a trademark of Rohm and Haas Co. Corp. of Philadelphia, Pa.), or charcoal, and then analytes are thermally desorbed or solvent extracted for analysis. See Riggin, "Compendium of Methods for the Determination of Toxic Organic Compounds in Ambient Air: Methods TO-1 and TO-2," U.S. Environmental Protection Agency, Research Triangle Park, N.C. 27711, EPA 600/4-84-041, April 1984; Winberry, et al., "Compendium of Methods for the Determination of Toxic Organic Compounds in Ambient Air: Method TO-14, Second Supplement," U.S. Environmental Protection Agency, Research Triangle Park, N.C. 27711, EPA 600/4-89-018, March 1989; Anon., "Compendium of Methods for the Determination of Toxic Organic Compounds in Ambient Air, Second Edition: Method TO-17," U.S. Environmental Protection Agency, Cincinnati, Ohio 45268, EPA/625/R-96/010b, January 1997. See also, Woolfenden, "Monitoring VOCs in air using sorbent tubes followed by thermal desorption-capillary GC analysis—Summary of data and practical guidelines," J. Air Waste Manage. Assoc. 47, 20-36 (1997); Pankow, et al., "Determination of a wide range of volatile organic compounds in ambient air using multisorbent adsorption/thermal desorption and gas chromatography/mass spectrometry," Anal. Chem. 70, 5213-21 (1998); Ciccioli, et al., "GC Evaluation of the Organic Components Present in the Atmosphere at Trace Levels with the Aid of Carbopack B for Preconcentration of the Sample," J. Chrom. 351, 433-49 (1986); Brown, et al., "Collection and Analysis of Trace Organic Vapour Pollutants in Ambient Atmospheres: The Performance of a Tenax-GC Adsorbent Tube," J. Chrom. 178, 79-90 (1979); Walling, "The Utility of Distributed Air Volume Sets When Sampling Ambient Air Using Solid Adsorbents," Atmos. Environ. 18, 855-59 (1984); and U.S. Pat. No. 4,541,268.

When used in conjunction with gas chromatography, an absorption tube is heated to rapidly desorb the retained analytes and produce a concentrated analyte pulse that is injected into a gas chromatography column. In such a method, the pre-concentrator tube serves a dual purpose of sample pre-concentration and injection. The different components in the sample are then chromatographically separated and analyzed by a detector. Gas chromatography is one common detection and measurement technique in which a gas sample containing analytes of interest is introduced into a flowing stream of a carrier gas and pumped through a capillary, the wall of which is coated with a stationary phase material. The analytes partition between the moving carrier gas and the stationary phase by absorbing and desorbing from the coating as they migrate through the capillary. The components are thus separated according to their relative partition coefficients and they exit the capillary at different times. Analytes with similar physical and chemical properties may thus be efficiently separated. A detector that is chosen based on the type of gases being analyzed is positioned at the outlet of the capillary and constantly measures the gas mixture as it exits. Exemplary detectors include thermal conductivity, electron capture, flame ionization, mass spectrometry, and chemiluminescence detectors.

Sorbent-based gaseous analyte pre-concentration methods have several disadvantageous features. For example, low gas permeability of sorbent materials requires sampling of high gas volumes. The sorbent material may be inadvertently overloaded. If the sorbent is highly retentive of an adsorbed trace material, then it will require relatively large elution volumes. Also, the analyte may react with the sorbent material or the material itself may cause introduction of interfering contaminants that compromise the analytical data. There is the added disadvantage of the time required to regenerate (or replace and condition) the chemical sorbent or membrane, and carry out the gas-chromatographic separation prior to detection, which limits output. Unless the pre-concentrator tube is heated for a sufficiently long time, all of the accumulated analytes may not be released, and the sample of chemical released from the sorbent material that reaches the detector may not accurately reflect the concentration of chemical entering the sorbent material. Furthermore, the sorbent may exhibit a memory effect in which chemicals remaining in the sorbent material are released when the pre-concentrator tube is heated a subsequent time, thereby producing artificially higher measurements. In order to measure analytes present in concentrations below about 1 ppb in air, a relatively large volume of sorbent, which requires large elution volumes, may be required, and in such cases some substances (particularly non-volatile trace materials) that bind very strongly may be difficult to desorb.

As an alternative to sorbent-based pre-concentration methods, "cryofocusing" (or "thermofocusing") may be used to pre-concentrate analytes from a gas sample in a thermal focusing chamber or cold trap. Cryofocusing is the concentration of analytes by condensing them out of their original gas matrix into a smaller volume in an inert tube. A typical cold trap is a capillary tube enveloped by a cold vessel that is chilled. In such a device, a gas sample is passed through the capillary and, by exposing incoming analyte to the low temperatures, it condenses within the capillary. When sufficient amounts of analyte have been accumulated, the temperature of the capillary passing through the cold trap is rapidly increased to volatilize the sample. A carrier gas stream that continually flows through the trap then injects the analyte into the column for separation. Pankow, et al., "Determination of volatile compounds in water by purging directly to a capillary column with whole column cryotrapping," Environ. Sci. Technol. 22, 398-405 (1988); U.S. Pat. Nos. 5,005,399, 5,595,709, 5,795,368, 5,954,860, 5,872,306; Ewels, et al., "Electrically Heated Cold Trap Inlet System for High-Speed Gas Chromatography," Anal. Chem. 57, 2774-79 (1985); Mouradian, et al., "Evaluation of a Nitrogen-Cooled, Electrically Heated Cold Trap Inlet for High-Speed Gas Chromatography," J. Chrom. Sci. 28, 643-48 (1990); Klemp, et al., "Cryofocusing Inlet with Reverse Flow Sample Collection for Gas Chromatography," Anal. Chem. 65, 2516-21 (1993); Tijssen, et al., "Theoretical Aspects and Practical Potentials of Rapid Gas Analysis in Capillary Gas Chromatography," Anal. Chem. 59, 1007-15 (1987); and Giese, et al., "Adsorption/thermal desorption for the determination of volatile organic compounds in water," J. Chrom. 537, 321-28 (1991).

In the past, cryofocusing has typically been accomplished by cooling the sample gas stream to liquid nitrogen temperatures. The analytes can then be transferred to the column by flash heating. Often, the sample is then "refocused" at the head of the column. By combining cryofocusing methods with sorbent-based techniques in a trap, a similar effect can be achieved with trapping at ambient temperatures.

Although some of the shortcomings discussed above respecting sorbent-based pre-concentration methods are overcome by thermal focusing techniques, a number of disadvantages persist. As a practical matter, cryogenic methods of pre-concentration are limited by small sample volumes (about 10 mL or less). Also, the use of thermal focusing with a gas chromatography system produces undesirable dead volume and band broadening which adversely affect system resolution and efficiency. After heating the cold trap sample tube, the sample components must traverse the entire length of the sample tube before introduction into the column. As the length of time that the sample is injected at the inlet end of the column increases, the peaks produced by elution of the components tend to broaden.

The requirement of application of heat in both sorbent-based pre-concentration methods and thermal focusing methods is a significant limitation. Certain compounds thermally degrade upon heating at temperatures required for thermal desorption or GC separations. Therefore, these methods are not ideally used in the analysis of thermal sensitive compounds. In GC thermal focusing, analytes may be exposed to excessive temperatures in order to volatilize them entirely through the focusing chamber, thereby causing thermal decomposition. Instead of actual analytes of the original sample being ejected from the column, these components become fragmented, which significantly complicates analysis. Furthermore, the entire length of the cold trap sample tube cannot be maintained ideally at a uniform constant temperature, either during the collection or injection modes, and a thermal gradient exists. Because during the collection mode of operation, the analyte condenses near the inlet end of the capillary tube, making it necessary to insure that region is sufficiently heated to volatilize all of the component during the injection step. This requirement leads to some portions of the cold trap sample tube being heated to a significantly higher temperature than is necessary to volatilize the sample collected.

SUMMARY OF THE INVENTION

The present invention provides analytical methods, instruments, and devices that address the shortcomings addressed above. The present invention provides a device, system, and associated methods that will actively or passively sample air by directing it onto the surface of a porous semiconductor substrate, for example a desorption/ionization on porous silicon ("DIOS") chip. Because the porous silicon has both high surface area and an active surface with excellent adsorptive properties, the inventors have found it is an ideal surface for adsorbing certain chemicals from air. In addition, once the adsorption step is complete, the surface can be analyzed directly by laser desorption/ionization by placing the chip into a matrix-assisted laser desorption/ionization-time of flight ("MALD-TOF") mass spectrometer. [0]However, as opposed to traditional MALDI, there is no need to add a UV absorbing organic matrix, since the silicon acts to absorb the UV energy, giving rise to the desorption/ionization process.

Because the process of laser desorption/ionization and mass detection of the components from the porous silicon surface does not require the elevated temperatures of prior art systems, thermal degradation of the components is avoided. Thus, the invention provides for the adsorption of components contained in a gas, for example, ambient air, without the need for applied heat that may cause thermal degradation of analytes.

Accordingly, the invention provides methods for sampling and analysis of gas samples to determine the chemical compounds thereof at low concentrations. The invention also includes methods of monitoring a gas, e.g., ambient air, for the amounts of chemicals therein. In another aspect, the invention relates to active or passive gas-sampling devices, including devices that can be located in relatively small or remote areas.

In one embodiment, the invention provides a method for detecting an analyte contained in a gas comprising the steps of directing a gas comprising an analyte onto the surface of a porous semiconductor substrate (particularly a "porous silicon substrate," as defined herein) for a period of time sufficient for the analyte to be adsorbed onto the surface; and the analyzing the analyte by laser desorption/ionization.

Similarly, the invention includes a method for detecting an analyte contained in a gas comprising the steps of providing a porous light-absorbing semiconductor substrate; directing a gas comprising an analyte onto the semiconductor substrate for a period of time sufficient for an analyte contained in the gas to be adsorbed onto the semiconductor substrate; and then analyzing the analyte by laser desorption/ionization.

In yet another aspect, the invention provides a method for analyzing a physical property of an analyte comprising obtaining a porous light-absorbing semiconductor substrate; contacting a quantity of a gas containing an analyte having a physical property to be determined with the semiconductor substrate to form an analyte-loaded semiconductor substrate, wherein the analyte is adsorbed directly from the gas; and irradiating the analyte-loaded semiconductor substrate to produce an ionized analyte or a product resulting from the chemical reaction thereof.

Another embodiment of the invention provides a method for providing an analyte ion suitable for analysis of a physical property thereof involving providing a porous light-absorbing semiconductor substrate having a multiplicity of saturated carbon atoms covalently bonded to the semiconductor substrate; contacting a quantity of a gas containing an analyte having a physical property to be determined with the semiconductor substrate to form an analyte-loaded semiconductor substrate; placing the analyte loaded-semiconductor substrate under reduced pressure; and irradiating the analyte-loaded semiconductor substrate with an ultraviolet or infrared laser source under reduced pressure to provide an ionized analyte that is suitable for analysis to determine a desired physical property.

Another method of the invention provides for identifying an analyte ion, the method comprising providing a porous, light-absorbing, silicon semiconductor substrate with a porosity of about 60% to about 70% with ethyl phenyl groups bonded thereto; contacting a quantity of a gas containing an analyte having a mass to be analyzed with the semiconductor substrate to form an analyte-loaded semiconductor substrate, wherein the gas is free of matrix molecules; applying a potential of about ±5,000 to about ±34,000 volts to the analyte-loaded semiconductor substrate; irradiating the analyte-loaded semiconductor substrate under reduced pressure with an ultraviolet laser to provide an ionized analyte; and analyzing the mass to charge ratio of the ionized analyte by time-of-flight mass spectrometry techniques.

The invention also includes devices and instruments for use in the methods of the invention. For example, the invention includes a device for active sampling of a gas and directing the same gas onto a porous, preferably light-absorbing, semiconductor substrate comprising a gas conduit having an inlet end and an outlet end; a nozzle having an inlet end and an outlet end, wherein the conduit outlet end and the nozzle inlet end are fluidly connected, wherein the nozzle is capable of directing a gas from the conduit outlet end, through the nozzle, and onto a porous light-absorbing semiconductor substrate; and a pump for introducing the gas through the conduit inlet end and moving the gas through the nozzle outlet end.

The invention also provides a device for passive sampling of a gas. The device comprises a DIOS etched surface with a protective cover over the top, which would allow air to come in contact with it. An example of such a device comprises an upper cover having a plurality of parallel walls projecting downwardly from the upper cover that form a series of channels; a lower plate having a plurality of parallel walls projecting upwardly from the lower plate that form a series of channels; and a surface of porous light-absorbing semiconductor substrate located at a distal end of the lower plate, wherein the surface faces the upper cover; wherein the upper plate and the lower plate are spaced apart form each other such that the respective parallel walls interdigitate, thereby creating a series of baffles that allow gas to flow to the distal end of the lower plate and contact the surface.

DETAILED DESCRIPTION OF THE INVENTION

Figure 1:
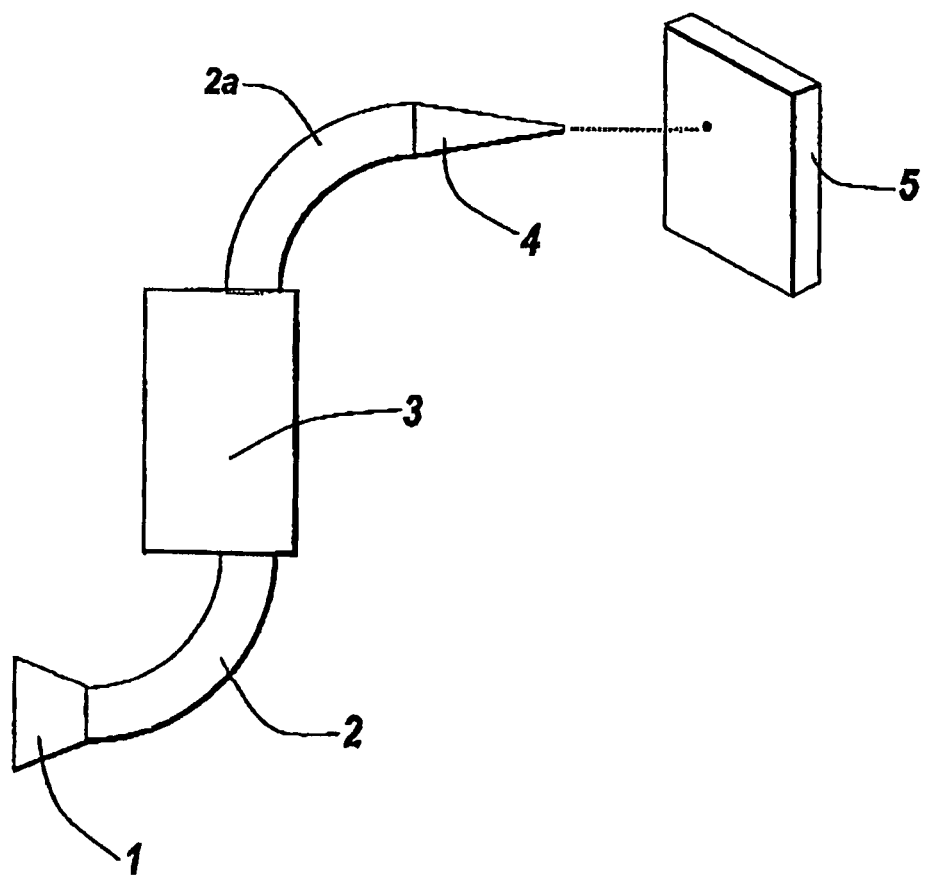
FIG. 1 illustrates an active air sampling device in accordance with the invention, where ambient air is sampled from an inlet end of an intake and pumped through a nozzle which is directed at the porous silicon surface of a DIOS chip.

The invention relates to the collection and analysis of components of gas samples, especially components present in trace quantities. For convenience, some definitions of terms referred to herein are set forth below.

As used herein, the term "gas" is meant to include broadly any non-condensed phase, including the gaseous phases of materials that are ordinarily regarded as liquids and solids at room temperature and pressure. A gas may be any of the gaseous forms of a material at a particular temperature and pressure, regardless of whether that form is thermodynamically or kinetically preferred. As such, a gas may include certain constituent compounds that are not ordinarily considered gases per se but that are capable of being adsorbed onto a semiconductor substrate from an air stream or the like. A gas may behave as an ideal thermodynamic gas or a non-ideal thermodynamic gas. A gas may be made by sublimation or evaporation of a solid or liquid, or it may be made by atomizing a liquid into very small particles or droplets.

A gas may be an aerosol, cloud, fume, mist, fog, plume, or smoke. An "aerosol" is generally regarded as a mixture or dispersion of discrete small particles (solid or liquid of about 0.01 μm to about 100 μm in diameter) and a carrier gas (usually air) that is at least partially stabile in the earth's gravitational field. Similarly, a "cloud" is merely an aerosol that is dense enough to be perceptible to the eye. A "fume" is similar to an aerosol, but usually refers to solid particles resulting from the condensation of vapor from a chemical reaction. On the other hand, a "mist" or "fog" is qualitatively a suspension of liquid droplets in a gas. A "plume" usually refers to the gaseous and aerosol effluents emitted by combustion. "Smoke" is a visible aerosol of particles resulting from the incomplete combustion, e.g., of organic matter such as fossil fuels, and typically consists of carbon, carbon-rich products, and all other dispersible product particles from the incomplete combustion (but generally not including steam or condensed water vapor). As the present invention relates to methods of analyzing any of these types of materials, the terms gas, aerosol, cloud, fume, mist, fog, plume, and smoke may be used interchangeably unless otherwise indicated.

"Ambient air" includes the outdoor or indoor air in a particular location. Ambient air may include the components of pure air and air pollutants. The composition of pure air depends on the particular location, and is variable in its components (e.g., methane, carbon dioxide, water) so "pure" air has no precise meaning. Nevertheless, pure air is commonly considered to be air which is free of dust, aerosols, and reactive gaseous contaminants of anthropogenic origin (i.e., man-made). The composition of the major components in dry air is relatively constant (percent by volume given): nitrogen 78.08; oxygen 20.95; argon 0.93; carbon dioxide 0.03; neon 0.0018; helium 0.00052; methane 0.00016, krypton 0.00011; hydrogen 0.00005; nitrous oxide 0.00003; xenon 0.000009. Relative clean air which is free of most reactive anthropogenic pollution often used as a reference sample in the calibration and operation of instruments may be purchased under the designation of "zero air."

An air "pollutant" or "pollution" is typically a substance, gaseous material, or aerosol that has been introduced into the air (either by human activity or by natural processes). Typically an air pollutant produces a measurable adverse or undesirable effect on humans, animals, vegetation, or materials (monuments, etc.) when present in sufficient concentration, and may interfere with comfort, health or welfare of persons or the environment.

The term "passive" as in "passive sampling" means that analytes are collected from a gas sample by molecular diffusion without a specific controlled conveyance of the gas. The term "active" is the opposite of "passive" and means that a gas sample and analytes therein are specifically conveyed in a controlled manner.

An "analytical" instrument or unit or "analyzer" is an assembly of sub-units comprising suitable apparatus permitting the introduction and removal of a sample gas to be analyzed; a measuring cell or other apparatus that produces signals (e.g., electrical signals in the form of a chromatogram or spectrogram) from the physical or chemical properties of the components of the sample gas, allowing their identification or measurement; and signal processing devices (amplification, recording) or, if need be, data processing devices. A measuring cell typically is a "detector," which is an instrument or part of an instrument that indicates the presence of a compound by means of some specific spectroscopic or chemical property thereof.

A "mass spectrometer" is an analyzer used in chemical analysis that operates by ionizing atoms or molecules and then measuring the relative mass of the ionized products. Mass spectrometry ("MS") is routinely used to measure the molecular weight of a sample molecule, as well as the fragmentation characteristics of a sample to identify that sample. Mass spectrometry measures the ratio of the mass of the molecule to the ion's electric charge. The mass is customarily expressed in terms of atomic mass units, called Daltons. The charge or ionization is customarily expressed in terms of multiples of elementary charge. The ratio of the two is expressed as a "m/z" ratio value (mass/charge or mass/ionization ratio). Because the ion usually has a single charge, the m/z ratio is usually the mass of the "molecular ion," or its molecular weight ("MW").

One way of measuring the mass of the sample accelerates the charged molecule, or ion, into a magnetic or electric field. The sample ion moves under the influence of the magnetic or electric field. A detector can be placed at the end of the path through the magnetic field, and the m/z of the molecule calculated as a function of the path through the magnetic field and the strength of the magnetic field. A variety of different mass analyzers known in the art may be used, such as quadrupole, triple quadrupole, sector, FTMS, TOF, ion traps, e.g., linear quadrupole ion traps and 3-dimensional ion traps, and quadrupole-TOF hybrid, among others.

MS may be carried out in the gas phase in which an electrically neutral sample at low pressure is passed through an electron beam. The simplest mass spectrometers introduce a gaseous, electrically neutral sample in vacuo, normally at pressures of about $10^{-6}$ Torr or less. In this MS technique, an electron beam strikes the sample and ejects one or more electrons after which the sample is ionized with a net positive charge. The ionized sample is then passed through a magnetic field and, depending on the course of the ionized sample through that field, the mass of the molecule to the ion's electric charge is measured.

Another technique for measuring the mass of the sample is time-of-flight ("TOF") mass spectrometry. In TOF-MS, a sample ion is accelerated by a known voltage, and the time it takes a sample ion or fragment thereof to travel a known distance is measured. Mass spectrometry is used to measure the mass of a sample molecule, as well as the mass of the fragments of a sample to identify that sample.

Molecules that are not readily put in the gaseous phase are more difficult to analyze by MS. Several techniques exist for volatilizing samples, including high molecular weight. When a sample molecule is deposited on a substrate, the sample is said to be adsorbed to that substrate. Desorption occurs when a molecule adsorbed on a substrate is removed from the substrate. Instead of starting with a gas phase sample, as in basic MS, desorption MS may be applied to a sample adsorbed on a substrate.

One desorption MS technique is matrix-assisted laser desorption/ionization ("MALDI"). In accordance with this technique, a sample is ionized by transferring a proton from an organic matrix to the sample as part of the volatilization process. Ionization of the sample is achieved by electron beam ionization or proton transfer ionization.

In a typical MALDI experiment, a sample is mixed into a light-absorbing organic matrix that vaporizes upon pulsed laser radiation, carrying the sample with the volatilized matrix. Although it is a widely used and powerful technique, MALDI is not generally appropriate for the study of small molecules because the matrix interferes with measurements below a m/z of about 700. MALDI also has significant limitations in the analysis of large molecules because, for example, the matrix can form adducts with the sample ion and thereby interfere with the analysis.

Newer MS techniques permit a direct laser desorption/ionization technique in the absence of a matrix. Such methods include ionization of an analyte on a semiconductor substrate, particularly a "porous silicon substrate" or a "porous light-absorbing silicon substrate," by irradiating the analyte-loaded substrate under reduced pressure, including methods commonly known as "desorption/ionization on silicon" ("DIOS"). "Porous silicon substrates" and "porous light absorbing silicon substrates" are known in the art, see, e.g., U.S. Pat. Nos. 6,288,390 and 6,358,613, particularly in the microelectronics arts.

Although many methods may be used to produce porous silicon substrates, electrochemical etching is among the most common. Y. Watanabe, et al., Rev. Electron. Commun. Labs. 19, 899 (1971); and R. C. Anderson, et al., J. Microelectro-Mechanical System 3, 10 (1994). These electrochemically etched porous silicon substrates are characterized by being the result of a wet electrochemical etching process involving sequential formation of the silicon itself (or obtaining it from a commercial source) and then wet etching. A substrate thus formed typically has pore regions that are more interconnected with greater etching.

The term "porous silicon substrate" or more generally "porous semiconductor substrate" as used herein refers to a semiconductor material (e.g., silicon) having a surface appropriate for accepting (by adsorption) analytes and absorbing electromagnetic radiation (therefore a "semiconductor substrate" may also be referred to as a "light-absorbing semiconductor substrate"). As described more fully elsewhere herein, porous silicon substrates may be conventional silicon wafers or thin film silicon that has been etched. For example, an electrochemical wet etching process involves exposing the silicon to a wet solution and passing a current through a contact to the etching sample and through the solution (e.g., an aqueous or alcoholic hydrofluoric acid solution) thereby producing a "pitting" or etching of the metal leaving a porous network structure. In "electrochemical" (or "anodic") etching, the microstructure (e.g., pore size, morphology, and spacing) as well as the porous silicon substrate layer thickness are controlled by the resistivity of the silicon itself, the current and potential, the electrolyte composition, and the ambient light, temperature, and other reaction conditions. The silicon may be an etched continuous single crystal or a single crystal wafer, or polycrystalline silicon. Such methods are described further herein and are well known in the art. L. T. Canham, Appl. Phys. Lett. 57, 1046 (1990); I. Schecter, et al., Anal. Chem. 67, 3727 (1995); J. Wei, et al., Nature 399, 243 (1999); L. T. Canham, et al., Thin Sold Films 297, 304 (1997); P. Steiner, et al., and Thin Solid Films 255, 52 (1995).

Such porous silicon substrates were heretofore believed to be poor substrates for the sampling and retention (and analysis) of analytes from ambient air. One exemplary alternative approach requires the use of plasma-enhanced chemical vapor deposition or physical vapor deposition to produce films of different morphologies, described as either "continuous void-free" films or "columnar/void network" films. The deposition methods entail gas-phase metal chemistry with its attendant complications. The resulting products are silicon arrays having a nanoscale columnar/void network structure. U.S. 2002/0048531 A1. Such columnar/void network films have not been widely accepted, however.

Because of the absorptivity of the semiconductor substrate, the substrate acts as an energy receptacle for electromagnetic radiation. This absorbed electromagnetic energy is used to ionize the trapped analyte. The ionized analyte is then detected by mass spectrometry mass analyzing apparatus. A preferred desorption/ionization method for mass spectrometry is pulsed laser desorption/ionization from a porous silicon substrate, and therefore such methods are usually called "desorption/ionization on porous silicon" ("DIOS") mass spectrometry, whether or not the semiconductor substrate is silicon-based. Although embodiments of the invention are described herein in terms of certain preferred embodiments employing a silicon-based substrate, the term "DIOS" is meant to embrace functionally equivalent materials notwithstanding, unless otherwise stated. Amato, et al., Optoelectronic Properties of Semiconductors and Superlattices (Eds. Amato, G., Delerue, C. & Bardeleben, H.-J.v.) 3-52 (Gordon and Breach, Amsterdam, 1997); Canham, Appl. Phys. Lett. 57, 1046 (1990); Cullis, et al., Appl. Phys. Lett. 82, 909 (1997). For example, a common semiconductor substrate is silicon-bonded with hydrophobic groups, e.g., ethyl phenyl groups. Further examples are exemplified elsewhere herein. In a typical DIOS-MS experiment, a sample is placed on a semiconductor substrate and then irradiated with ultraviolet light, optionally with an applied voltage. The benefit of such methods is that the use of a matrix is not required, so that the methods are more amenable to small molecule analysis. Additionally, the semiconductor substrate may be chemically or structurally modified to optimize the desorption/ionization characteristics of the substrate. See also, Shen, et al., Anal. Chem., 73, 612-19 (2001); Thomas, et al., Proc. Nat. Acad. Sci. U.S.A. 98, 4932-37 (2001); and Kruse, et al., Anal. Chem. 73, 3639-45 (2001). Certain aspects of the present invention may be described in chemical terms.

Unless otherwise stipulated, the meanings of chemical moieties referred to herein may be ascertained by reference "Nomenclature of Organic Chemistry, Sections A, B, C, D, E, F, and H," Pergamon Press, Oxford, 1979. IUPAC.

According to the present invention, "alkyl groups" include saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or cycloalkyl or alicyclic groups) (e.g., cyclopropyl, cyclopentyl, cyclohexyl, cycloheptyl, cyclooctyl, etc.), branched-chain alkyl groups (isopropyl, tert-butyl, sec-butyl, isobutyl, etc.), and alkyl-substituted alkyl groups (e.g., alkyl-substituted cycloalkyl groups and cycloalkyl-substituted alkyl groups). The term "aliphatic group" includes organic moieties characterized by straight or branched-chains, typically having between 1 and 22 carbon atoms. In complex structures, the chains may be branched, bridged, or cross-linked. Aliphatic groups include alkyl groups, alkenyl groups, and alkynyl groups In certain embodiments, a straight-chain or branched-chain alkyl group may have 30 or fewer carbon atoms in its backbone, e.g., $C_1$-$C_{30}$ for straight-chain or $C_3$-$C_{30}$ for branched-chain. In certain embodiments, a straight-chain or branched-chain alkyl group may have 20 or fewer carbon atoms in its backbone, e.g., $C_1$-$C_{20}$ for straight-chain or $C_3$-$C_{20}$ for branched-chain, and more preferably 18 or fewer. Likewise, preferred cycloalkyl groups have from 4-10 carbon atoms in their ring structure, and more preferably have 4-7 carbon atoms in the ring structure. The term "lower alkyl" refers to alkyl groups having from 1 to 6 carbons in the chain, and to cycloalkyl groups having from 3 to 6 carbons in the ring structure.

Unless the number of carbons is otherwise specified, "lower" as in "lower aliphatic," "lower alkyl," "lower alkenyl," etc. as used herein means that the moiety has at least one and less than about 8 carbon atoms. In certain embodiments, a straight-chain or branched-chain lower alkyl group has 6 or fewer carbon atoms in its backbone (e.g., $C_1$-$C_6$ for straight-chain, $C_3$-$C_6$ for branched-chain), and more preferably 4 or fewer.

Likewise, preferred cycloalkyl groups have from 3-8 carbon atoms in their ring structure, and more preferably have 5 or 6 carbons in the ring structure. The term "$C_1$-$C_6$" includes alkyl groups containing 1 to 6 carbon atoms. Moreover, unless otherwise specified the term alkyl includes both "unsubstituted alkyls" and "substituted alkyls," the latter of which refers to alkyl moieties having substituents replacing one or more hydrogens on one or more carbons of the hydrocarbon backbone. Such substituents may include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or aromatic or heteroaromatic moieties.

An "arylalkyl" moiety is an alkyl group substituted with an aryl (e.g., phenylmethyl (i.e., benzyl)). An "alkylaryl" moiety is an aryl group substituted with an alkyl group (e.g., p-methylphenyl (i.e., p-tolyl)). The term "n-alkyl" means a straight-chain (i.e., unbranched) unsubstituted alkyl group. An "alkylene" group is a divalent moiety derived from the corresponding alkyl group. The terms "alkenyl" and "alkynyl" refer to unsaturated aliphatic groups analogous to alkyls, but which contain at least one double or triple carbon-carbon bond respectively. Suitable alkenyl and alkynyl groups include groups having 2 to about 12 carbon atoms, preferably from 1 to about 6 carbon atoms.

The term "aromatic group" or "aryl group" includes unsaturated cyclic hydrocarbons containing one or more rings. Aryl groups may also be fused or bridged with alicyclic or heterocyclic rings which are not aromatic so as to form a polycycle (e.g., tetralin). The term "aromatic group" includes unsaturated cyclic hydrocarbons containing one or more rings. In general, the term "aryl" includes groups, including 5- and 6-membered single-ring aromatic groups that may include from zero to four heteroatoms, for example, groups derived from benzene, pyrrole, furan, thiophene, thiazole, isothiaozole, imidazole, triazole, tetrazole, pyrazole, oxazole, isooxazole, pyridine, pyrazine, pyridazine, and pyrimidine, and the like. An "arylene" group is a divalent moiety derived from an aryl group. The term "heterocyclic group" includes closed ring structures in which one or more of the atoms in the ring is an element other than carbon, for example, nitrogen, sulfur, or oxygen. Heterocyclic groups may be saturated or unsaturated and heterocyclic groups such as pyrrole and furan may have aromatic character. They include fused ring structures such as quinoline and isoquinoline. Other examples of heterocyclic groups include pyridine and purine. Heterocyclic groups may also be substituted at one or more constituent atoms The term "amino," as used herein, refers to an unsubstituted or substituted moiety of the formula —$NR^aR^b$, in which $R^a$ and $R^b$ are each independently hydrogen, alkyl, aryl, or heterocyclyl, or $R^a$ and $R^b$, taken together with the nitrogen atom to which they are attached, form a cyclic moiety having from 3 to 8 atoms in the ring. Thus, the term "amino" includes cyclic amino moieties such as piperidinyl or pyrrolidinyl groups, unless otherwise stated. Thus, the term "alkylamino" as used herein means an alkyl group, as defined above, having an amino group attached thereto. Suitable alkylamino groups include groups having 1 to about 12 carbon atoms, preferably from 1 to about 6 carbon atoms. The term "alkylthio" refers to an alkyl group, as defined above, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group, as defined above, having a carboxyl group attached thereto. The term "alkoxy" as used herein means an alkyl group, as defined above, having an oxygen atom attached thereto. Representative alkoxy groups include groups having 1 to about 12 carbon atoms, preferably 1 to about 6 carbon atoms, e.g., methoxy, ethoxy, propoxy, tert-butoxy and the like. The term "nitro" means —$NO_2$; the term "halogen" or "halo" designates —F, —Cl, —Br or —I; the term "thiol," "thio," or "mercapto" means SH; and the term "hydroxyl" or "hydroxyl" means —OH.

Unless otherwise specified, the chemical moieties of the compounds of the invention, including those groups discussed above, may be "substituted or unsubstituted." In some embodiments, the term "substituted" means that the moiety has substituents placed on the moiety other than hydrogen (i.e., in most cases, replacing a hydrogen) which allow the molecule to perform its intended function. Examples of substituents include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., —$NH_2$), $(CR'R'')_{0-3}CN$ (e.g., —CN), —$NO_2$, halogen (e.g., —F, —Cl, —Br, or —I), $(CR'R'')_{0-3}C(halogen)_3$ (e.g., —$CF_3$), $(CR'R'')_{0-3}CH(halogen)_2$, $(CR'R'')_{0-3}CH2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., —$SO_3H$), $(CR'R'')_{0-3}O(CR'R'')_{0-3}H$ (e.g., —$CH_2OCH_3$ and —$OCH_3$), $(CR'R'')_{0-3}S(CR'R'')_{0-3}$ H (e.g., —SH and —SCH$_3$), (CR'R")$_{0-3}$OH (e.g., —OH), (CR'R")$_{0-3}$COR', (CR'R")$_{0-3}$ (substituted or unsubstituted phenyl), (CR'R")$_{0-3}$(C$_3$-C$_8$ cycloalkyl), (CR'R")$_{0-3}$CO$_2$R' (e.g., —CO$_2$H), or (CR'R")$_{0-3}$OR' group, or the side chain of any naturally occurring amino acid; wherein R' and R" are each independently hydrogen, a C$_1$-C$_8$ alkyl, C$_2$-C$_5$ alkenyl, C$_2$-C$_5$ alkynyl, or aryl group, or R' and R" taken together are a benzylidene group or a —(CH$_2$)$_2$O(CH$_2$)$_2$— group.

A "substituent" as used herein may also be, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety.

The invention, therefore, provides a method for detecting an analyte contained in a gas comprising directing a gas comprising an analyte onto the surface of a porous semiconductor substrate for a period of time sufficient for the analyte to be adsorbed onto the surface; and analyzing the analyte by laser desorption/ionization.

The present invention exploits the capacity of a semiconductor substrate such as a DIOS chip to extract analytes directly from a gaseous sample such as ambient air Without intending to be bound by theory, the invention exploits the following phenomenon. Because DIOS-MS substrates are hydrophobic, compounds in a sample that are also hydrophobic may preferentially be partitioned onto the chip, although non-hydrophobic compounds may also be analyzed according to the invention. A similar partitioning between the gas phase and the adsorbed phase may also occur because of the relative rates of diffusion of gas molecules vs. analyte molecules.

A significant advantage of the present invention is the ability to forego sample pre-concentration or preparation, for example, cryofocusing, because the analytes are directly deposited from the gas sample on to, for example, a DIOS chip which then may be directly used in a MS instrument. A further advantageous aspect of the invention is the ability to analyze samples that may contain temperature-sensitive analytes. In accordance with the invention, desorption and ionization can be accomplished in a single step with a nitrogen, OPO, excimer, or infrared laser without heating at high temperatures, which are known to cause degradation of many compounds. Therefore, by eliminating the necessity of thermal desorption and gas-phase separation, the present invention provides greatly improved throughput. In cases where chromatography, such as GC and HPLC, are not needed, pre-column derivatization of reactive functional groups would also not be necessary, which is an additional advantageous feature of the invention.

One benefit of the present invention is the provision of a sensitive technique for desorption/ionization of molecules at picomole, femtomole, and attomole amounts. Another benefit of the present invention is that a substrate does not require the use of a matrix in order to ionize a sample. Because of the lack of a matrix, the measurement of m/z values is not complicated by the low-mass interference that a matrix normally involves. The reduced matrix interference also improves the measured peak height of the measured analyte as compared to the broadened and shortened peaks seen in MALDI measurements.

Yet another advantage of the present invention is the ease of chemically, and structurally modifying the substrate. This provides the ability to optimize the desorption/ionization characteristics of the substrate for biomolecular or other applications.

In one embodiment, the invention provides a method for detecting an analyte contained in a gas comprising providing a porous light-absorbing semiconductor substrate; directing a gas comprising an analyte onto the semiconductor substrate for a period of time sufficient for an analyte contained in the gas to be adsorbed onto the semiconductor substrate; and analyzing the analyte by laser desorption/ionization.

The invention also provides a method analyzing a physical property of an analyte comprising obtaining a porous light-absorbing semiconductor substrate; contacting a quantity of a gas containing an analyte having a physical property to be determined with the semiconductor substrate to form an analyte-loaded semiconductor substrate, wherein the analyte is adsorbed directly from the gas; and irradiating the analyte-loaded semiconductor substrate to produce an ionized analyte or a product resulting from the chemical reaction thereof.

In yet another embodiment, the invention provides a method for providing an analyte ion suitable for analysis of a physical property thereof comprising providing a porous light-absorbing semiconductor substrate having a multiplicity of saturated carbon atoms covalently bonded to the semiconductor substrate; contacting a quantity of a gas containing an analyte having a physical property to be determined with the semiconductor substrate to form an analyte-loaded semiconductor substrate; placing the analyte loaded-semiconductor substrate under reduced pressure; irradiating the analyte-loaded semiconductor substrate with an ultraviolet laser under reduced pressure to provide an ionized analyte that is suitable for analysis to determine a desired physical property.

Similarly, the invention includes a method for identifying an analyte ion, the method comprising providing a porous, light-absorbing, silicon semiconductor substrate with a porosity of about 60% to about 70% with ethyl phenyl groups bonded thereto; contacting a quantity of a gas containing an analyte having a mass to be analyzed with the semiconductor substrate to form an analyte-loaded semiconductor substrate, wherein the gas is free of matrix molecules; applying a positive voltage of about ±5,000 to about ±34,000 volts to the analyte-loaded semiconductor substrate; irradiating the analyte-loaded semiconductor substrate under reduced pressure with an ultraviolet laser to provide an ionized analyte; and analyzing the mass to charge ratio of the ionized analyte by time-of-flight mass spectrometry techniques.

The analyte may be hydrophobic and adsorbed onto and retained by the porous semiconductor substrate. The quantity of the analyte adsorbed onto the porous semiconductor substrate is less than about 1 millimole, or less than about 1 micromole, or even less than about 1 nanomole. Prior to analysis, the analyte typically need not be mixed with a light-absorbing matrix, such as light-absorbing organic polymers commonly used in MALDI. Analytes that are readily ionized are more easily analyzed by mass spectrometry. The gas containing analytes may be ambient air or any composition that is naturally a gas a room temperature and pressure. The gas may be a suspension of fine particulates, a smoke, a fog, or a nebulized suspension. The analyte may be a pollutant of anthropogenic origin, such as smoke or another pollutant, including components thereof. In one embodiment, the smoke is cigarette smoke, automobile engine exhaust, or fossil fuel combustion products. The analyte may also be a drug of abuse, a chemical warfare agent, or an explosive, or components thereof. The gas may be sampled directly from the environment or the gas may be in an air sampling container or bag, having been drawn into the air sampling container or bag using a vacuum pump.

In one embodiment of the invention, the semiconductor substrate is oxidized. In another embodiment of the invention, the semiconductor substrate is porous. In yet another embodiment of the invention, the semiconductor substrate is bonded with a substance having a saturated carbon atom bonded to the substrate.

A preferred embodiment of the invention has a porous semiconductor substrate, the surface of which is bonded with ethyl phenyl groups. In yet another embodiment of the invention, the semiconductor substrate is a porous semiconductor substrate having a hydrophobic surface coating. In a still further embodiment of the invention, the semiconductor substrate is a porous semiconductor substrate having a hydrophilic surface coating. In a still another embodiment of the invention, the semiconductor substrate is a porous semiconductor substrate having a fluorophilic surface coating.

The porous semiconductor substrate is preferably a porous silicon substrate. The porosity of the porous silicon may be defined as the amount of silicon lost from the native state of bulk silicon due to anodization and etching. This gravimetric measure can be done by calculating an average density for the porous semiconductor layer and comparing that density to that of the original semiconductor. Porosity (expressed as a percentage)=10-100*(density of porous semiconductor layer/density of original semiconductor layer). Accordingly, a sample of porous semiconductor with a porosity of 45% is 45% void (empty) and 55% semiconductor (filled). Brumhead, et al., Electrochim. Acta (UK) 38, 191-97 (1993).

In accordance with certain embodiments of the invention, the porosity of the porous semiconductor substrate may be about 4% to about 100%, or about 50% to about 80%, or even about 60% to about 70%. In a preferred embodiment, the porosity is about 50% to about 80%. In another preferred embodiment, the porosity is about 60% to about 70%.

A porous semiconductor such as silicon is an effective substrate for the methods of the invention, regardless of whether the porous silicon is microporous, macroporous, or mesoporous. Microporous substrates are those having a dominant pore size of less than about 2 nanometers. Mesoporous substrates are those having a dominant pore size of about 2-50 nm. And macroporous substrates are those having a pore size of greater than about 50 nm. In preferred aspects, the morphology of the pore is similar to that of an etched material, in which a portion of the material has been removed (typically by an oxidative process) from a continuous (i.e., void-free) sample, such as a single crystal, as opposed to a material constructed by depositing atoms in a manner than produces columnar void structures.

Porosity may also be defined in terms of the specific surface area per mass or volume. The specific surface area can be expressed as either as a surface area per unit mass of porous semiconductor, or as a surface area per unit volume of the porous semiconductor, the two numbers being related by the density of the semiconductor material. In accordance with the invention, the specific surface area of porous silicon is typically approximately 1 meter squared per gram of porous silicon (or approximately 2 meters squared per cubic centimeter of porous silicon), to approximately 1000 meters squared per gram of porous silicon (or approximately 2300 meters squared per cubic centimeter of porous silicon). In one embodiment, the porous silicon surfaces have specific surface areas of about 200 to about 800 $m^2/g$ (450 to 1900 $m^2/cm^3$). In another embodiment, the porous silicon surfaces have specific surface areas of approximately 640 meters squared per gram of porous silicon (or approximately 1500 meters squared per cubic centimeter).

In certain embodiments, the present invention provides methods of ionizing an analyte absorbed on a porous, light absorbing, semiconductor substrate. Accordingly, when using a porous silicon substrate, a method of the invention may be referred to in terms of a preferred porous silicon embodiment, namely, desorption/ionization on silicon (DIOS).

Other conducting or semiconducting materials, such as metals and semimetals, that absorb light and are capable of transmitting the light energy to an analyte to ionize it are within the scope of the invention. Other semiconductors that exhibit strong UV absorption when prepared with a porous surface are within the scope of the invention including, including Group IV semiconductors (e.g., diamond), Group I-VII semiconductors (e.g., CuF, CuCl, CuBr, CuI, AgBr, and AgI), Group II-VI semiconductors (e.g., BeO, BeS, BeSe, BeTe, BePo, MgTe, ZnO, ZnS, ZnSe, ZnTe, ZnPo, CdS, CdSe, CdTe, CdPo, HgS, HgSe, and HgTe), Group III-V semiconductors (e.g., BN, BP, BAs, AlN, AlP, AlAs, AlSb, GaN, GaP, GaSb, InN, InAs, and InSb), sphaelerite structure semiconductors (e.g., MnS, MnSe, β-SiC, $Ga_2Te_3$, $In_2Te_3$, $MgGeP_2$, $ZnSnP_2$, and $ZnSnAs_2$), wurtzite structure compounds (e.g., NaS, MnSe, SiC, MnTe, $Al_2S_3$, and $Al_2Se_3$), I-II-$VI_2$ semiconductors (e.g., $CuAlS_2$, $CuAlSe_2$, $CuAlTe_2$, $CuGaS_2$, $CuGaSe_2$, $CuGaTe_2$, $CuInS_2$, $CuInSe_2$, $CuInTe_2$, $CuTlS_2$, $CuTlSe_2$, $CuFeS_2$, $CuFeSe_2$, $CuLaS_2$, $AgAS_2$, $AgAlSe_2$, $AgAlTe_2$, $AgGaS_2$, $AgGaSe_2$, $AgGaTe_2$, $AgInS_2$, $AgInSe_2$, $AgInTe_2$, and $AgFeS_2$). In addition, other well known substrates, such as $Al_2O_3$, SiC, GaP, $Si_{1-x}Ge_x$, Ge, GaAs, and InP, that are capable of absorbing radiation are within invention.

Typically, the porous semiconductor substrate is hydrophobic, and it comprises a metal or a semi-metal, for example silicon, preferably porous silicon. The porous semiconductor may be prepared by electrochemical or acidic etching of silicon, for example crystalline silicon. The porous semiconductor substrate may also be oxidized, or an n-type semiconductor or a p-type semiconductor.

Freshly etched porous silicon substrates are hydrophobic due to a metastable, silicon-hydride termination. The metastable silicon-hydride termination is inherently unstable in the presence of oxygen and is eventually oxidized in air to a silicon-oxide surface. The substrate may also be chemically oxidized. The silicon-hydride termination can also be changed through Lewis acid-mediated or light-promoted hydrosilylation reactions. These and other hydrosilylation reactions stabilize and functionalize porous silicon substrates. The coatings added via these hydrosilylation reactions generally serve to render the surface hydrophobic, but can be hydrophilic when the terminations exhibit chemically appropriate substituents. Because of the high stability of the hydrophobic, hydrosilylated substrates to aqueous media, such substrates can be reused repeatedly with little degradation. For example, substrates that are normally destroyed by strongly alkaline solutions can be boiled in them after being functionalized by the Lewis acid-mediated or light-promoted hydrosilylation techniques. Buriak, et al., J. Am. Chem. Soc. 120, 1339-40 (1998); and Stewart, et al., Angew. Chem. Int. Ed. 37, 3257-3261 (1998).

Porous semiconductor substrates may be prepared according to methods known in the art. For example, one preparation method includes preparing a porous substrate from a solid substrate, e.g., a semiconductor wafer, including a preferred embodiment of selectively preparing portions of a solid substrate as a porous substrate; and modifying the substrate with optional substrate terminations (or "coatings," "ligands," "modifications," or "monolayers") for the porous substrate.

Porous silicon for DIOS may be prepared from either n-type or p-type silicon.

Both n-type mesoporous and p-type microporous or mesoporous samples have been effective in generating useful ion signals.

Usually, as in the DIOS process, a porous silicon substrate is prepared from flat crystalline silicon. Undoped semiconductors may be prepared using light etching or simple chemical etching as is known to those skilled in the art. Cullis, et al., J. Appl. Phys. 82, 909 (1997); and Jung, et al., J. Electrochem. Soc. 140, 3046 (1993). The result of the galvanostatic etching procedure, porous silicon is a microns-thick porous layer with a nanocrystalline architecture that often exhibits bright photoluminescence upon exposure to UV light. Sailor, et al., Adv. Mater. 9, 783 (1997); and Canham, Appl. Phys. Lett. 57, 1046 (1990).

The semiconductor substrate may be modified to optimize the desorption/ionization characteristics of the substrate for particular applications, such as to prevent spreading of an analyte. Preferably, a porous silicon surface is modified with a termination, because modifying the porous surface is believed to improve the stability of the surface and improve the signal generated by the surface. Modifying the surface may be done by hydrosilylation with organic terminations to yield hydrophobic porous silicon that is stable to aqueous media. Such substrates may be reused repeatedly with little degradation.

Porous silicon substrates are generally considered to be inert to MS analysis conditions, and porous silicon material production is inexpensive and simple. Porous silicon features as small as 20 μm and 100 nm can be produced through standard optical techniques. Cullis, et al., J. Appl. Phys. 82, 909-65 (1997); Doan, et al., Appl. Phys. Lett. 60, 619-20 (1992); and Schmuki, et al., Phys. Rev. Lett. 80, 4060-4063 (1998). See also, Cullis, et al., J. Appl. Phys. 82, 909 (1997).

The porous silicon substrates may be prepared, for example, by coating, to provide substrates with hydrophobic, hydrophilic, or fluorophilic surfaces. Such surface coatings may consist of any non-metallic atoms, including carbon, hydrogen, nitrogen, phosphorous, germanium, sulfur, fluorine, iodine, chlorine, bromine, phosphorous, boron, and selenium. In one preferred embodiment, a hydrophobic surface coating comprises saturated carbon atoms covalently bonded to the metal, for example a metal substrate covalently bonded with ethyl phenyl groups.

Porous silicon substrates may have a variety of surface terminations, for example, hydrogen (i.e., the native state), dodecyl, ethyl phenyl, and oxide. In one embodiment, the more hydrophobic surfaces, e.g., ethyl phenyl terminated surface.

In another embodiment, the invention provides porous silicon substrates having a surface comprising a covalently bound monolayer. Porous silicon provides a high surface area, and therefore is uniquely suited for use in sensor construction and electrometric sensing of analytes in test solutions. Porous silicon, however, has been known to be unstable to a wide variety of conditions. The mild reaction conditions associated with the use of solvent-soluble Lewis acids in accordance with the method of the invention provides a stable porous silicon surface.

In one embodiment, the surface coating is a covalently-bonded monolayer on the surface of the silicon, wherein the monolayer comprises a chemical moiety according to any of the formulae:

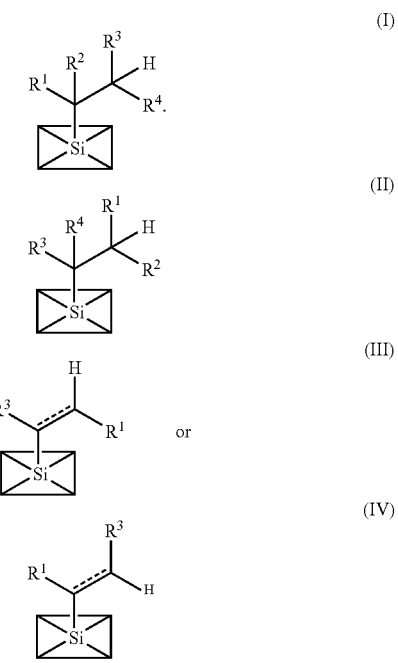

wherein
Si is a surface silicon atom;
‑ ‑ ‑ ‑ ‑ represents a double bond of either E- or Z-configuration;
$R^1$, $R^2$, $R^3$, and $R^4$ are each independently selected from the group consisting of hydrogen, substituted or unsubstituted alkyl or cycloalkyl, substituted or unsubstituted aryl or heteroaryl, and substituted or unsubstituted heterocyclic groups; provided that none of $R^1$, $R^2$, $R^3$, or $R^4$ has an alkenyl or alkynyl group; or
two geminal or vicinal R groups together with the carbon atoms to which they are attached form a cycloalkyl, cycloalkenyl, or heterocyclic ring.

The invention includes methods wherein either $R^1$ or $R^3$ is a phenyl group, and the remaining R groups are all hydrogen.

Thus, one advantage of the invention is that it allows formation of a surface-protecting monolayer under relatively mild conditions, i.e., at room temperature. The invention also provides a method whereby the surface of the porous silicon can be both protected and selectively functionalized with moieties or functional groups that can interact, for example, in some electrometrically detectable manner with predetermined analytes in a test fluid.

The method of the invention can also be carried out with mixtures of alkynes and alkenes to provide covalently bound surfaces wherein the mole fraction of the groups in the monolayer correspond generally to the mole fractions of the alkynes or olefins in the reagent mixture used to form the monolayer. The method of the invention can also be carried out with mixtures of alkynes and alkenes to provide covalently bound surfaces wherein the mole fraction of the groups in the monolayer correspond generally to the mole fractions of the alkynes or olefins in the reagent mixture used to form the monolayer.

An alkyne of the form $R^1C\equiv CR^2$ or an olefin of the form $R^1R^2C=R^3R^4$ may be attached to the porous silicon surface, wherein the R groups may be any independently, hydrogen or a substituted or unsubstituted alkyl, aryl, or heteroaryl group, in which R group substituents include substituents from the group consisting of $(C_1-C_{24})$ alkoxy, hydroxy, halo, cyano, ester, a primary or secondary or tertiary amino, carbamido, thiol, alkylthio, or two R groups together with the carbon atoms to which they are attached form a 5- or 6-membered ring. The R groups may also be any alkenyl group substituent as defined herein.

Accordingly, examples of porous silicon include those that have been hydrosilylated with the alkyne. $(R^1C\equiv CR^2)$ where $R^1$ is hydrogen, and $R^2$ is —$(CH_2)_9CH_3$ (from 1-dodecyne), —$(CH_2)_8COOCH_3$ (from methyl 10-undcynoate), -phenyl (from phenylacetylene), -tert-butyl (from tert-butylacetylene), —$(CH_2)_3CN$ (from 5-cyano-1-pentyne), —$(CF_2)_7CF_3$, —$(CH_2)_2OH$ (from 3-butyn-1-ol). Further examples of porous silicon include those that have been hydrosilylated with an olefin $(R^1R^2C\equiv R^3R^4)$ where $R^2$, $R^3$, and $R^4$ are hydrogen, and $R^1$ was $(CH_2)_5CH_3$ (from 1-hexene). Porous silicon has also been known to be hydrosilylated with an olefin where $R^1$, $R^2$, and $R^3$ are all methyl groups and $R^4$ is hydrogen (from 2-methyl-2-butene). The hydrosilylated porous silicon with the methyl ester terminated R group was mildly hydrophilic, and the porous silicon modified with the hydroxy terminated alkyl group, and the nitrile terminated alkyl group were both strongly hydrophilic. The other terminations were hydrophobic. The alkyne attaches as an olefin in an anti-Markovnikov addition with the porous silicon covalently bonded to one side of the new double bond and a hydrogen bonded on the other side to form a new cis double bond. In the case of the olefin, the carbon bearing the hydrogen covalently bonds to the porous silicon surface and the other end of the double bond gains a hydrogen. The result of reacting the porous silicon with an olefin is the formation of a coated substrate having silicon bonded to a saturated carbon atom, whereas reaction of porous silicon with an alkyne forms a coated substrate having silicon bonded to an unsaturated carbon atom. Accordingly, the silicon surface may be modified to be hydrophilic, hydrophobic, or fluorophilic, as appropriate for the intended end use.

Alternatively, covalently bound monolayers comprising mixtures of covalently bound species can be formed by sequentially reacting the surface with less than stoichiometric amounts of alkene or alkyne reactants. Functional groups present on the covalently bound monolayer, e.g., hydroxy, amino, carboxy and thiol, can be used to functionalize the surface further by coupling to biologically significant molecules using standard ester or amide-forming coupling techniques.

The porous semiconductor substrate usually is affixed to a support structure that is a solid-phase composition comprising silicon or an oxide thereof, a glass, an organic and inorganic polymer, a metal or semimetal, a ceramic, or a combination thereof. The porous semiconductor substrate may form one continuous layer on the support structure, or two or more discrete areas or patches on the support structure. The support structure may be substantially planar or particulate, in which case the support structure may be affixed to a second support structure or used as a free particulate material. Preferably, the support structure is silicon, oxidized silicon, or a combination thereof.

Once a sample containing analyte has been introduced (or loaded or deposited) to a suitable semiconductor substrate, the analyte is ready for desorption and ionization. The desorption and ionization of the analyte requires a source of electromagnetic radiation. The source of electromagnetic radiation provides radiation that the semiconductor substrate can absorb and use to desorb and ionize the analyte, to produce an ionized analyte or a product resulting from the chemical reaction thereof.

Certain methods of the invention include irradiating a porous semiconductor substrate with electromagnetic radiation. The methods may also include first placing the porous semiconductor substrate under a vacuum, and then irradiating while the semiconductor substrate is under the vacuum. The electromagnetic radiation may be produced from a nitrogen-UV, infrared, excimer, or OPO laser source. Upon irradiation, desorption occurs under reduced pressure or at approximately atmospheric pressure. Irradiating a porous semiconductor substrate with electromagnetic radiation causes desorption and ionization of the analyte(s) to produce an ionized analyte or a product resulting from the chemical reaction thereof.

The temperature at which the desorption/ionization occurs ideally is below the temperature at which the analyte would thermally degrade, and therefore the present invention is a significant advancement of the state of the art as discussed above.

In one embodiment of the invention, the analyte-loaded semiconductor substrate is irradiated with a laser. For a porous silicon substrate, the source of electromagnetic radiation is preferably an ultraviolet pulse laser. It is also preferable that the ultraviolet pulse laser be focused on the portion of the semiconductor substrate containing the analyte.

In a still further embodiment of the invention, the analyte-loaded semiconductor substrate is irradiated with ultraviolet light. In a yet still further embodiment of the invention, the analyte-loaded substrate is irradiated with light having a wavelength of approximately 337 nm. In yet another embodiment of the invention, a positive voltage is applied to the analyte-loaded semiconductor substrate. In a still further embodiment of the invention, a voltage of about 5,000 to about 30,000 volts is applied to the analyte-loaded semiconductor substrate. Another method of illuminating the sample uses laser shots from a 337 nm pulsed nitrogen laser (Laser Science, Inc.), with a power of 2 to 50 µJ/pulse, with a lens, and with an optional neutral density filter. Those skilled in the art will appreciate that a variety of difference lasers (producing light of varying wavelengths) may be used in the methods of the invention.

When performing mass spectrometry, an electric field is established between the porous semiconductor substrate and the detector, with a potential difference that is positive or negative with respect to the porous semiconductor substrate and ground. In general, the potential difference will depend on the particular device used and/or the orientation of the analyte relative to the electric field. Typically, the potential difference ranges from about ±5000 to about ±30,000 volts.

For example, the semiconductor substrate containing the analyte is held at a positive voltage during illumination, although with the appropriate changes the same method could be carried out in negative ion mode also. The positive voltage relative to the rest of the spectrometer is used to direct positive ions away from the substrate and toward the detector. Repelling the positive ions with positive voltage may be preferred because the ions are formed by proton transfer, for example, a voltage range for the substrate is from about +5,000 to about +30,000 volts (preferably approximately +20,000 volts). Other configurations may also be used in which the substrate or conductive sample plate is held at ground potential and then the ions are extracted and accelerated to high potential. An exemplary configuration includes an ion source, a plate and a DIOS chip that is at ground potential, and an applied extraction field, in which ions are accelerated to a high kinetic energy (e.g., "Micromass M@LDI" instrument, which is an "axial" MALDI time-of-flight instrument), or in which a relatively low voltage (e.g., about 0 to about 200 volts) is applied and the ions are collisionally cooled and then introduced into a pulser region of an orthogonal time-of-flight mass analyzer.

A mass analyzer having a time-of-flight detector is the preferred detector for measuring the desorbed and ionized analyte, and even more preferably, the time-of-flight mass analyzer is preceded by an ion reflector to correct for kinetic energy differences among ions of the same mass. Another optional enhancement of the time of flight mass analyzer is realized when there is a short, controlled, delay between the desorption and ionization of the analyte and the application of the initial acceleration voltage by the mass analyzer. Another optional embodiment of the invention uses the ion reflector to perform post source decay measurements on the desorbed, ionized, and reflected analyte. Other mass analyzers, including magnetic sector, single quadrupole, triple quadrupole, ion traps, e.g., linear ion traps and 3-dimensional ion traps, orthogonal time-of-flight, time-of-flight/time-of-flight tandem, and hybrid combinations of these mass analyzers, magnetic ion cyclotron resonance instruments, deflection instruments, and quadrupole mass analyzers are within the scope of the invention.

In one embodiment, the invention provides a DIOS-based monitoring system coupled with either on-line or off-line laser desorption/ionization mass spectrometers. A number of mass spectrometry systems are simple in design, compact, and portable enough to be used on site. With such portable systems, a DIOS-based sampling and analysis method of the invention may be carried out entirely outside of the laboratory setting. In another embodiment of the invention, samples are adsorbed to disposable, one-time use DIOS targets, and then returned to the laboratory setting for analysis.

Because the invention utilizes DIOS system based on a laser desorption/ionization time-of-flight mass spectrometry, one embodiment of the invention provides a compact, simple, and easy to use system ideally suited for portable air monitoring. The system provided by the invention does not require the use of noble gases (such as helium for a GC or hydrogen for an FID detector), and is designed with low power consumption in mind, as it would not require high power heating elements.

In a preferred embodiment, the determined physical property is mass, and a method for determining a physical property of an analyte ion analyzes the mass to charge ratio (m/z) of the analyte ion or ion fragment by mass spectrometry techniques. Similarly, methods of the invention may include a step of analyzing, which in some embodiments is the measurement of the mass to charge ratio (m/z) of the analyte ion or ion fragment by mass spectrometry techniques.

The analyzing step comprises determining or measuring a physical property of the analyte; preferably the analyzing step is quantitative. In certain embodiments, the quantitative analysis is carried out with reference to an internal standard. The physical property is the mass to charge ratio of an ion produced by the ionization of the analyte as measured by a mass spectrometry technique. In certain embodiments, the ion produced by ionization of the analyte is a molecular ion of the analyte. The term "molecular ion" as used herein includes, but is not limited to, protonated species, deprotonated species, molecular ion adducts (e.g., alkali metal adducts such as sodium, potassium, and lithium adducts), etc. In other embodiments, the ion produced by ionization of the analyte is a fragment ion of the analyte.

The mass analyzer used in the mass spectrometry technique may be selected from the group consisting of an orthogonal time-of-flight mass analyzer, ion traps, e.g., 3-dimensional ion traps (e.g., Finnegan LCQ Deca XP MAX®, available from Thermo Electron Corporation, Woburn, Mass.), linear ion traps (e.g., Finnegan LTQ®, available from Thermo Finnegan Corporation, Woburn, Mass., and Q TRAP® and 4000 Q TRAP® LC/MS/MS systems available from Applera Corporation, Norwalk, Conn.) single quadrupole, triple quadrupole, Fourier transform MS, magnetic sector, quadrupole-TOF hybrid, or time-of-flight/time-of-flight tandem, ion mobility mass spectrometer, and hybrid combinations thereof. Furthermore, the mass spectrometer may be operated in either a positive or negative mode; for example, the porous semiconductor substrate may be may be either positive or negative with respect to ground.

The invention also embraces the devices used in the methods described herein. Therefore, the invention pertains to a device for active sampling of a gas and directing the same gas onto a porous light-absorbing semiconductor substrate comprising a gas conduit having an inlet end and an outlet end; a nozzle having an inlet end and an outlet end, wherein the conduit outlet end and the nozzle inlet end are fluidly connected, wherein the nozzle is capable of directing a gas from the conduit outlet end, through the nozzle, and onto a porous light-absorbing semiconductor substrate; and a pump for introducing the gas through the conduit inlet end and moving the gas through the nozzle outlet end. The pump may be disposed between and fluidly connected to the conduit outlet end and the nozzle inlet end. Likewise, the pump may be positioned at the conduit inlet end so as to push the gas through the conduit inlet end and through the nozzle outlet end. In another embodiment, the pump further comprises a tube having an inlet end and an outlet end, and wherein the tube inlet end is fluidly connected to the pump and the tube outlet end is positioned relative to the conduit inlet end so as to introduce gas pumped through the tube to the conduit inlet end. Also, the device may further comprise a porous light-absorbing semiconductor substrate, wherein the semiconductor substrate is positioned relative to the nozzle outlet end, so that the gas pushed through the nozzle outlet end is directed onto the semiconductor substrate. In some cases, the semiconductor substrate is sealed in a vessel suited for receiving the gas by a pump.

The invention also includes devices for passive sampling of a gas comprising an upper cover having a plurality of parallel walls projecting downwardly from the upper cover that form a series of channels; a lower plate having a plurality of parallel walls projecting upwardly from the lower plate that form a series of channels; and a surface of porous light-absorbing semiconductor substrate located at a distal end of the lower plate, wherein the surface faces the upper cover; wherein the upper plate and the lower plate are spaced apart form each other such that the respective parallel walls interdigitate, thereby creating a series of baffles that allow gas to flow to the distal end of the lower plate and contact the surface, optionally with a protective cover that does not substantially inhibit gas flow.

Certain illustrative embodiments of the invention will be described with reference to FIGS. 1-4. FIG. 1 depicts a device in accordance with the invention for direct sampling of ambient air onto a DIOS chip. Ambient air is introduced into the inlet end of gas intake 1 by the action of pump 3. The inlet end of pump 3 is fluidly connected to the outlet end of gas intake 1 by hose 2. The outlet end of pump 3 is fluidly connected to the inlet end of nozzle 4 by hose 2a. Pump 3 then pushes the ambient air thought tube 2a and through the outlet end of nozzle 4. A DIOS chip 5 having a porous silicon surface (produced by photochemical etching of the chip) is positioned relative to the outlet end of the nozzle 4 such that the ambient air pumped through the nozzle is directed to the porous silicon surface of DIOS chip 5, thereby allowing components in the air to be adsorbed and concentrated onto the porous silicon surface.

Figure 2:
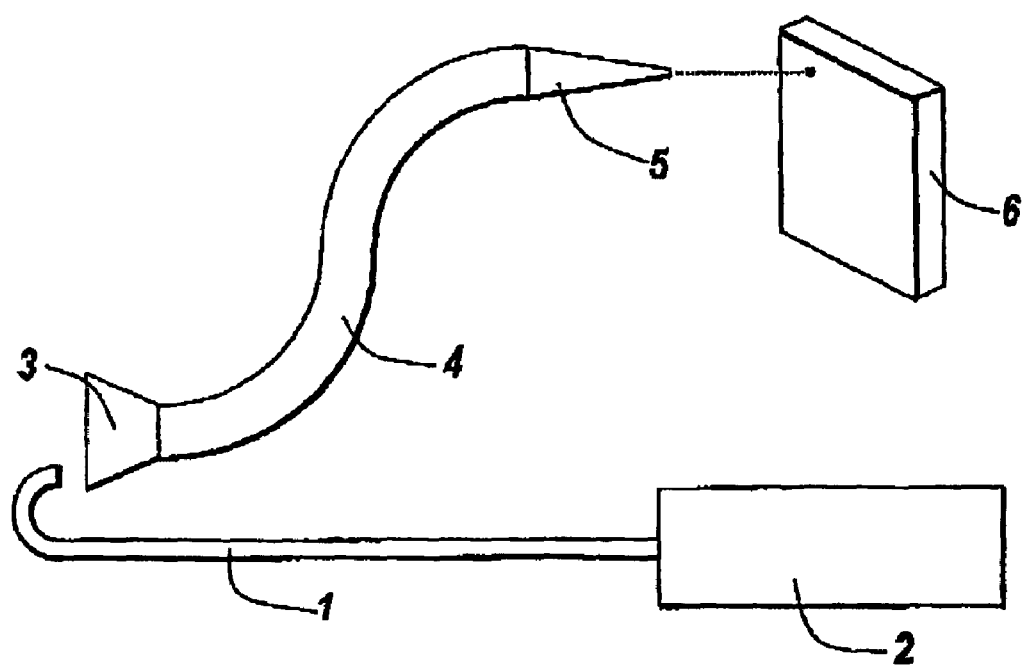
FIG. 2 illustrates another embodiment of an active air sampling device in accordance with invention, where ambient air is pumped and directed to the inlet end of an intake.

FIG. 2 depicts another embodiment of the device in accordance with the invention for direct sampling of ambient air onto a DIOS chip. In accordance with the "entrainment" approach depicted in FIG. 2, the outlet end of gas intake 3 is directly and fluidly connected to the inlet end of nozzle 5 by hose 4. The outlet end of pump 2 is fluidly connected to the inlet end of J-tube 1. The J-shaped outlet end of J-tube is positioned near the inlet end of gas intake 3, such that ambient air is pumped into the inlet end of gas intake 3, through connecting tube 4 and through nozzle 5. Again, A DIOS chip 6 having a porous silicon surface (produced by photochemical etching of the chip) is positioned relative to the outlet end of the nozzle 5 such that the ambient air pumped through the nozzle is directed to the porous silicon surface of DIOS chip 6, thereby allowing components in the air to be adsorbed onto the porous silicon surface.

Figure 3:
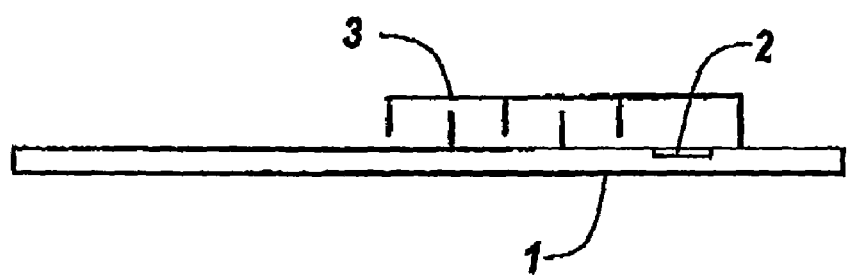
FIG. 3 illustrates a passive, direct air sampling device in accordance with the invention.

FIG. 3 depicts a passive ambient air sample device in accordance with the invention. In this embodiment, a DIOS chip 1 is provided with a plurality of upwardly protruding walls to create a plurality of U-shaped channels. At the distal end of the DIOS chip is a porous silicon surface contained on the DIOS chip. A cover 3 is provided with a plurality of downwardly protruding walls to create a plurality of U-shaped channels. Cover 3 is positioned over DIOS chip 1 so that the outer most downwardly protruding wall of the cover is adjacent to the porous silicon surface and makes contact with the surface of the DIOS chip but not with the porous silicon surface. The other, opposite outermost downwardly protruding wall as well as the remaining downwardly protruding walls are of a length such that they do not contact the surface of the DIOS chip, leaving an airflow space between the ends of these walls and the surface of the DIOS chip. Cover 3 is also positioned relative to DIOS chip 1, so that the upwardly protruding walls of the DIOS chip and the downwardly protruding walls of cover 3 are interdigitated, creating a baffle structure that permits ambient air to travel through the baffles and make contact with the porous silicon surface at the distal end of DIOS chip 1.

Figure 4:
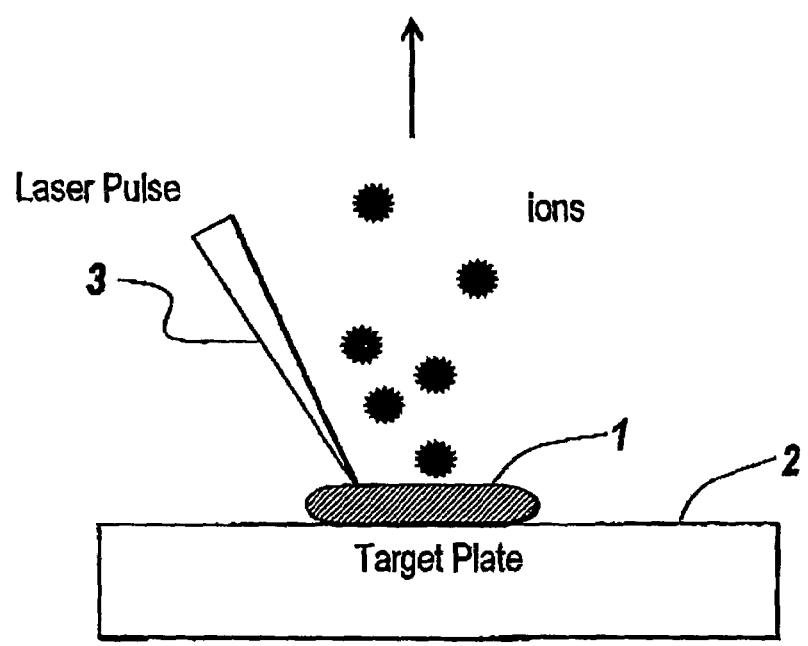
FIG. 4 illustrates a DIOS chip loaded onto a target plate where components of ambient air adsorbed onto the porous silicon surface of the DIOS chip (using any of the devices illustrated in FIGS. 1-3) are desorbed and ionized with a laser pulse and detected, for example, by a time-of-flight mass spectrometer.

FIG. 4 depicts a DIOS chip 1, on which has been adsorbed components of ambient air using any one of the devices depicted in FIGS. 1-3. The DIOS chip is shown mounted on sample target plate 2 and exposed to a laser pulse 3 that desorbs and ionizes the components from the DIOS chip.

Gas-sampling devices of the invention may be coupled with either an on-line or an off-line laser desorption/ionization mass spectrometer. The device (and the corresponding methods) may therefore be coupled with either an on-line or an off-line laser desorption/ionization mass spectrometer, or the mass spectrometer is portable, miniaturized, or suited for field-based use. For convenient field-based analysis, the porous light-absorbing semiconductor substrate may be disposable, or the porous light-absorbing semiconductor substrate may used to collect an analyte in the field, and then returned to the laboratory setting for analysis.

The present invention also relates to an apparatus for providing an ionized analyte for analysis. The apparatus has a semiconductor substrate. The apparatus also has a source of radiation or is capable of accepting a radiation-emitting device. When the source of radiation irradiates the semiconductor substrate under reduced pressure and an analyte is adsorbed on the substrate, the irradiation can cause the desorption and ionization of the analyte for analysis.

In one embodiment, the invention includes a "bag sampling" device (e.g., Supelco model number: 1060, 1062, or 1063, Bellefonte, Pa., USA), in which a DIOS chip is placed in a bag and then a vacuum is created inside a surrounding container that draws the air to be sampled into the bag, without the air ever coming in contact with the air pump itself.

In another embodiment of the invention, the analyte-loaded semiconductor substrate is placed under reduced pressure before irradiation. The reduced pressure can vary substantially depending on the sensitivity desired. Pressures of about $10^{-6}$ Torr to $10^{-7}$ Torr are typical in many varieties of mass spectrometry. Less reduced pressures can be used, up to $10^{-2}$ Torr, although probably with reduced sensitivity as the pressure rises (A higher pressure is desirable in the source region of an orthogonal-TOF instrument in order to provide collisional cooling/focusing of ions prior to their introduction into the TOF mass analyzer.). On the other hand, for an axial TOF mass analyzer for example, lower reduced pressures may provide benefits to sensitivity, and pressures as low as $10^{-11}$ Torr are possible. However, the sensitivity improvements realized by using extremely reduced pressures rarely justify the inconvenience and expense of use of additional or larger vacuum pumps.

The present invention is useful in the monitoring of gases to detect whether or not they contain various gaseous species of interest, as well as for the purpose of detecting and identifying various constituents of a gas to be monitored. The present invention is ideally suited for air monitoring of pollutants (e.g., amines, nitrogen heterocycles, etc.), drugs of abuse, chemical warfare agents (e.g., organophosphorous, organoarsenic) explosives, etc. The invention can also be used for air monitoring for process quality assurance/quality control, diagnostic purposes (e.g., automobile exhaust), as well as air sampling for contaminants (e.g., components in second hand cigarette smoke, formaldehyde in "sick building syndrome," etc.). Other applications include process stream monitoring, environmental monitoring, and engine exhaust gas analysis. Yet another application is in monitoring hazardous wastes escaping from landfills domestic, industrial, commercial, and military origin.

Detectable analytes include, for example, those generated by the manufacture of food, industrial agents, or chemical products. Examples of such analytes include food additives (e.g., bulking agents, vitamins, colorants or flavorants), agrichemicals (such as pesticides, insecticides, herbicides, and fertilizers), surfactants (e.g., sodium dodecylsulfate), adhesives (e.g., isocyanate glues), resins (e.g., wood resins and epoxy resins), organic pollutants, and process chemicals (e.g., chemicals used in water systems) such as flocculating polymers, biocides, corrosion inhibitors, anti-scalants, solvents, and compounds produced there from.

The invention is well suited for use in process control and environmental monitoring applications. Examples of environmental pollutants that may be analyzed according to the invention include, for example, pesticides, PCBs, and dioxins. The methods of the invention may also be applied in the detection and analysis of polycyclic aromatic hydrocarbons (PAHs), known to be carcinogenic or mutagenic, examples of which include pyrene, benz(a)anthracene, chrysene, benzo(a)pyrene, benzo(b)fluoranthene, benzo(k)fluoranthene, benzo(g,h,i)perylene, dibenz(a,h)anthracene, anthracene, phenanthrene, acenaphthene, acenaphthylene, benzo(e)pyrene, fluoranthene, fluorene, ideno(1,2,3-cd)pyrene, naphthalene, perylene, and coronene. One skilled in the art will appreciate that the present invention is most advantageously applied to the analysis of these compounds that are more readily ionizable.

The present invention may also be used in the detection of "drug of abuse" or "street drugs," including illicit or illegal drugs. Drugs of abuse are used principally for recreational purposes or in satisfaction of an addiction, and are often self-administered or administered without the oversight of a competent healthcare provider. Drugs of abuse also include therapeutic drugs that have a high potential for addiction or abuse, such as steroids, sedatives, antidepressants, and other mood-altering drugs. Drugs of abuse may be available by prescription, but subject to abuse or addiction. Examples of drugs of abuse include diuretics (e.g., acetazolamide, amilonde, bendroflumethiazide, bumetanide, canrenone, chlormerodrin, chlorthalidone, diclofenamide, ethacrynic acid, furosemide, hydrochlorothiazide, mersalyl, spironolactone, and triamterene), narcotic analgesics (e.g., alphaprodine, anileridine, suprenorphine, codeine, dextromoramide, dextropropoxyphene, diamorphine, dihydrocodeine, dipipanone, ethoheptazine, ethylmorphine, levorphanol, methadone, morphine, nalbuphine, pentazocine, pethidine, phenazocine, and trimeperidine), and β-blockers (e.g., acebutolol, alprenolol, atenolol, labetalol, metoprolol, nadolol, oxprenolol, propanolol, and sotalol). Examples of drugs of abuse also include stimulants (e.g., amfepramone, amphetamine, amphetaminil, amiphenazole, benzphetamine, benzoylecgonine, caffeine, cathine, chlorphentermine, clobenzorex, clorprenaline, cocaine, cotinine, cropropamide, crotethamide, dimethamphetamine, ephedrine, etafedrine, ethamivan, etilamphetamine, fencamfamin, fenethylline, fenproporex, furfenorex, mefenorex, methamphetamine, methoxyphenamine, methylephedrine, methylenedioxymethamphetamine, methylphenidate, morazone, nicotine nikethamide, pemoline, pentetrazol, phendimetrazine, phenmetrazine, phentermine, phenylpropanolamine, pipradrol, prolintane, propylhexedrine, pyrovalerone, strychnine, and theophylline). Further examples of drugs of abuse include hallucinogens (e.g., lysergic acid diethylamide, mescaline, phencyclidine, ketamine, dimethoxymethylamphetamine, tetrahydrocannabinol, marijuana, methylenedioxymethamphetamine), sedatives/hypnotics (e.g., chloral hydrate, glutethimide, meprobamate, and methaqualone), and anabolic steroids (e.g., bolasterone, boldenone, clostebol, dehydromethyltestosterone, fluoxymesterone, mesterolone, methandienone, methandrostenolone, methenolone, methyltestosterone, nandrolone, norethandrolone, oxandrolone, oxymesterone, oxymetholone, stanozolol, and testosterone). Additional examples of drugs of abuse include opiates (e.g., heroin, morphine, methandone, meperidine, codeine, propoxyphene, and acetylmorphine), barbiturates (e.g., amobarbital, pentobarbital, secobarbital, phenobarbital, butalbital, and butabartial), benzodiazepines (e.g., diazepam, clorazepate, chlordiazepoxide, oxazepam, flurazepam, lorazepam, alprazolam, and triazolam), antipsychotics-antidepressants (e.g., chlorpromazinc, trazodone, haloperidol, amoxapine, lithium carbonate, doxepin, imipramine, and amitriptyline), and analgesics (e.g., acetylsalicylic acid, acetaminophen, ibuprofen, diflunisal, and phenylbutazone).

In some circumstances, the invention may also be applied to the detection and measurement of therapeutic drugs. A "therapeutic drug" analyte is typically a drug or medicine administered for legitimate or medically-approved, therapeutic or diagnostic, purpose. Therapeutic drugs may available be over-the-counter or by prescription. Examples of therapeutic drugs include an adrenergic, anti-helmintic, anti-acne agent, anti-adrenergic, anti-allergic, anti-amebic, anti-androgen, anti-anemic, anti-anginal, anti-anxiety, anti-arthritic, anti-asthmatic, anti-atherosclerotic, antibacterial, anticholelithic, anticholelithogenic, anticholinergic, anticoagulant, anticonvulsant, antidepressant, antidiabetic, antidiarrheal, antidiuretic, antidote, anti-emetic, anti-epileptic, antiestrogen, antifibrinolytic, antifungal, antiglaucoma agent, antihemophilic, antihemorrhagic, antihistamine, antihyperlipidemic, antihyperlipoproteinemic, antihypertensive, antiinfective, anti-inflammatory, antimalarial, antimicrobial, antimigraine, antimitotic, antimycotic, antinauseant, antineoplastic, antineutropenic, antiobessional, antiparasitic, antiparkinsonian, antiperistaltic, antipneumocystic, antiproliferative, antiprotozoal, antipruritic, antipsychotic, antirheumatic, antischistosomal, antiseborrheic, antisecretory, antispasmodic, antithrombotic, antitussive, anti-ulcerative, anti-urolithic, and antiviral agents.

Further examples of therapeutic drugs include adrenocortical steroids; adrenocortical suppressant; alcohol deterrents; aldosterone antagonists; amino acids; ammonia detoxicants; anabolic steroids; analeptic agents: analgesics (e.g., lidocaine); androgens; anesthetics; anorectics; appetite suppressant; benign prostatic hyperplasia therapy agents; blood glucose regulators; bone resorption inhibitors; bronchodilators; carbonic anhydrase inhibitors; cardiac depressants; cardioprotectants; cardiotonics; cardiovascular agents; cholinergic agonist and antagonists; cholinesterase deactivators or inhibitors; coccidiostatic agents; cognition adjuvants and enhancers; depressants; diagnostic aids and contrast agents; diuretics; dopaminergic agents; ectoparasiticides; emetics; enzyme inhibitors; and estrogen.

Reference to analytes that are drugs is also intended to include the various metabolites and derivatives of the native drugs, which are often the primary substances detected, due to rapid metabolism of a drug in the body. Preferably, such analytes are volatile or, for example, found in the exhaled breath of a person known or suspected of using a particular drugs.

An analyte according to the present invention may also be an environmental toxin, industrial pollutant, industrial chemical, or other pollutants (e.g., amines, nitrogen heterocycles, etc.). Analytes may also be a chemical warfare agent (e.g., organophosphorous and organoarsenic compounds). Yet another application of the invention is in monitoring hazardous air-borne wastes escaping from landfills domestic, industrial, commercial, and military origin.

EXAMPLES

The invention is further illustrated by the following example, which should not be construed as further limiting.

Detection of Nicotine in Cigarette Smoke

Figure 5:
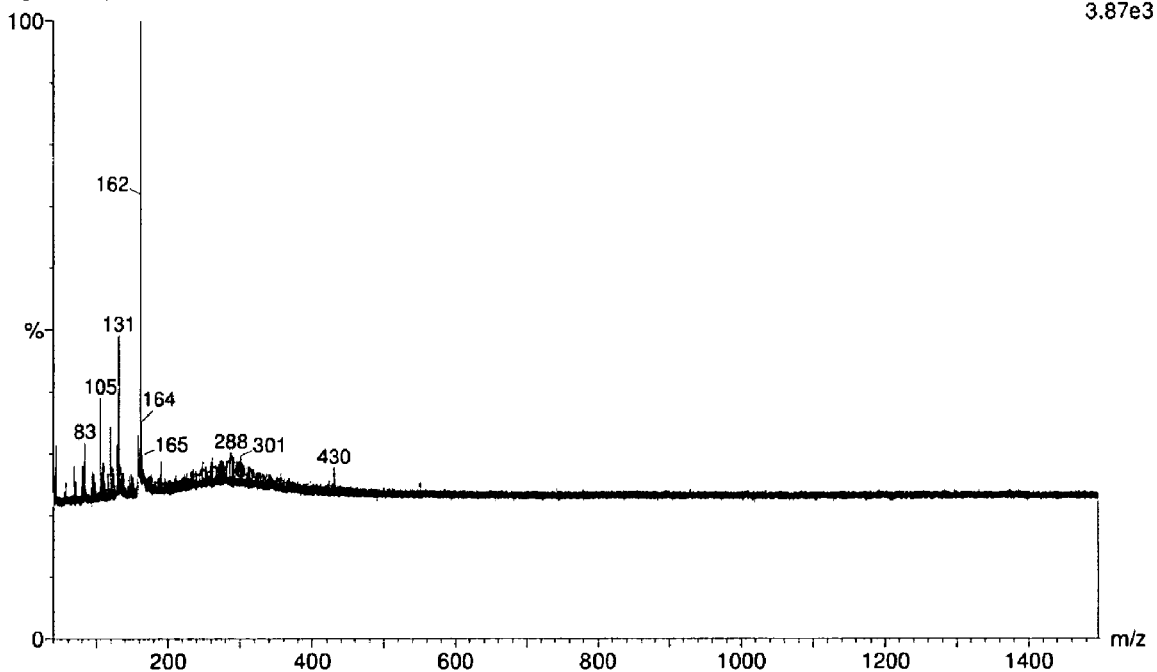
FIG. 5 illustrates the mass spectrum (TOF LD+) of a spot of cigarette smoke adsorbed onto a DIOS chip.

A lit cigarette was mounted in a glass holder (a short segment of glass cut from a disposable pipette) and connected to the side-arm of an Erlenmeyer flask by inert plastic tubing. The mouth of the flask was fitted with a rubber stopper through which a glass disposable pipette was inserted. The end of the pipette projecting out of the flask was connected to a diaphragm pump, thereby forming a closed system extending from the burning cigarette, through the chamber of the flask, and finally to the pump. The pump was engaged in order to draw smoke from the cigarette into the chamber. When sufficient smoke had been collected, the pump was disengaged and replaced with a source of compressed air, and the cigarette and the holder were replaced with a glass disposable pipette. Gas flow through the system was reversed and the trapped smoke was expelled from the flask under pressure. The smoke was directed onto a DIOS chip through the tapered end of the pipette so that individual spots of adsorbed material were formed. The spots were then analyzed by mass spectrometry (TOF LD+), and a strong nicotine signal was clearly visible at m/z=162. The spectrum is shown in FIG. 5.

The invention claimed is:

1. A method for detecting an analyte contained in a gas comprising:
   (a) directing a gas comprising an analyte onto the surface of a porous semiconductor substrate for a period of time sufficient for said analyte to be adsorbed onto said surface; and
   (b) analyzing said analyte by laser desorption/ionization.

2. The method of claim 1, wherein said porous semiconductor substrate is a porous silicon substrate.

3. The method of claim 1, wherein said porous semiconductor substrate is affixed to a support structure.

4. The method of claim 3, wherein said porous semiconductor substrate forms a continuous layer on said support structure.

5. The method of claim 3, wherein said porous semiconductor substrate forms two or more discrete areas on said support structure.

6. The method of claim 3, wherein said support structure is a solid-phase composition comprising silicon or an oxide thereof, a glass, an organic and inorganic polymer, a metal or semimetal, a ceramic, or a combination thereof.

7. The method of claim 6, wherein said support structure is silicon, oxidized silicon, or a combination thereof.

8. The method of claim 3, wherein said support structure is substantially planar or particulate.

9. The method of claim 8, wherein said particulate support structure is affixed to a second support structure.

10. The method of claim 9, wherein said second support structure is a solid-phase composition comprising silicon or an oxide thereof, a glass, an organic and inorganic polymer, a metal or semimetal, a ceramic, or a combination thereof.

11. The method of claim 1, wherein said porous semiconductor substrate absorbs light.

12. The method of claim 1, wherein said porous semiconductor substrate is a porous light-absorbing semiconductor substrate.

13. The method of claim 1, wherein said porous semiconductor substrate is microporous, macroporous, or mesoporous.

14. The method of claim 1, wherein the porosity of said porous semiconductor substrate is about 4% to about 100%.

15. A method for detecting an analyte contained in a gas comprising:
   (a) providing a porous light-absorbing semiconductor substrate;
   (b) directing a gas comprising an analyte onto said semiconductor substrate for a period of time sufficient for an analyte contained in said gas to be adsorbed onto said semiconductor substrate; and
   (c) analyzing said analyte by laser desorption/ionization.

16. A method for analyzing a physical property of an analyte comprising:
   (a) obtaining a porous light-absorbing semiconductor substrate;
   (b) contacting a quantity of a gas containing an analyte having a physical property to be determined with said semiconductor substrate to form an analyte-loaded semiconductor substrate, wherein said analyte is adsorbed directly from the gas; and
   (c) irradiating said analyte-loaded semiconductor substrate to produce an ionized analyte or a product resulting from the chemical reaction thereof.

17. A method for providing an analyte ion suitable for analysis of a physical property thereof comprising:
   (a) providing a porous light-absorbing semiconductor substrate having a multiplicity of saturated carbon atoms covalently bonded to the semiconductor substrate;
   (b) contacting a quantity of a gas containing an analyte having a physical property to be determined with said semiconductor substrate to form an analyte-loaded semiconductor substrate;
   (c) placing the analyte loaded-semiconductor substrate under reduced pressure;
   (d) irradiating said analyte-loaded semiconductor substrate with an ultraviolet laser under reduced pressure to provide an ionized analyte that is suitable for analysis to determine a desired physical property.

18. A method for identifying an analyte ion, the method comprising:
   (a) providing a porous, light-absorbing, silicon semiconductor substrate with a porosity of about 60% to about 70% with ethyl phenyl groups bonded thereto;
   (b) contacting a quantity of a gas containing an analyte having a mass to be analyzed with said semiconductor substrate to form an analyte-loaded semiconductor substrate, wherein said gas is free of matrix molecules;
   (c) applying a positive voltage of about ±5,000 to about ±34,000 volts to said analyte-loaded semiconductor substrate;
   (d) irradiating said analyte-loaded semiconductor substrate under reduced pressure with an ultraviolet laser to provide an ionized analyte; and
   (e) analyzing the mass to charge ratio of the ionized analyte by time-of-flight mass spectrometry techniques.

19. A device for active sampling of a gas and directing the same gas onto a porous light-absorbing semiconductor substrate comprising:
   (a) a gas conduit having an inlet end and an outlet end;
   (b) a nozzle having an inlet end and an outlet end, wherein said conduit outlet end and said nozzle inlet end are fluidly connected, wherein said nozzle is capable of directing a gas from said conduit outlet end, through said nozzle, and onto a porous light-absorbing semiconductor substrate; and
   (c) a pump for introducing said gas through said conduit inlet end and moving said gas through said nozzle outlet end.

20. A device for passive sampling of a gas comprising:
   (a) an upper cover having a plurality of parallel walls projecting downwardly from the upper cover that form a series of channels;
   (b) a lower plate having a plurality of parallel walls projecting upwardly from the lower plate that form a series of channels; and
   (c) a surface of porous light-absorbing semiconductor substrate located at a distal end of said lower plate, wherein said surface faces the upper cover;
      wherein said upper plate and said lower plate are spaced apart form each other such that the respective parallel walls interdigitate, thereby creating a series of baffles that allow gas to flow to the distal end of the lower plate and contact said surface, optionally with a protective cover that does not substantially inhibit gas flow.

* * * * *